(12) United States Patent
Karg

(10) Patent No.: US 11,376,024 B2
(45) Date of Patent: Jul. 5, 2022

(54) INTRAMEDULARY NAIL WITH RECEPATACLE FOR RECEIVING A TARETING DEVICE FOR TARGETING A BONE-ANCHOR FIXATION HOLE

(71) Applicant: DEPUY SYNTHES PRODUCTS, INC., Raynham, MA (US)

(72) Inventor: Nicholas Karg, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 280 days.

(21) Appl. No.: 16/570,299

(22) Filed: Sep. 13, 2019

(65) Prior Publication Data

US 2021/0077126 A1 Mar. 18, 2021

(51) Int. Cl.
*A61B 17/72* (2006.01)
*A61B 17/17* (2006.01)
*A61B 34/20* (2016.01)
*A61B 17/56* (2006.01)

(52) U.S. Cl.
CPC ...... *A61B 17/1725* (2013.01); *A61B 17/7241* (2013.01); *A61B 17/7283* (2013.01); *A61B 34/20* (2016.02); *A61B 2017/564* (2013.01); *A61B 2034/2051* (2016.02)

(58) Field of Classification Search
CPC ...... A61B 17/72–7275; A61B 17/7283; A61B 17/17; A61B 17/1717; A61B 17/1725; A61B 17/1707; A61B 34/20; A61B 2090/3954; A61B 2090/3958; A61B 2090/397; A61B 2090/3975
See application file for complete search history.

(56) References Cited

U.S. PATENT DOCUMENTS

| 6,616,670 B2 | 9/2003 | Simon et al. |
| 7,060,075 B2 | 6/2006 | Govari et al. |
| 8,814,868 B2 | 8/2014 | Janna et al. |
| 9,539,037 B2 | 1/2017 | Janna et al. |
| 2005/0096655 A1* | 5/2005 | Trinchese ............... A61B 17/72 606/62 |
| 2008/0086145 A1 | 4/2008 | Sherman et al. |

(Continued)

FOREIGN PATENT DOCUMENTS

| EP | 2380514 A1 | 10/2011 |
| WO | 2007/125497 A1 | 11/2007 |

*Primary Examiner* — Eduardo C Robert
*Assistant Examiner* — Michelle C Eckman
(74) *Attorney, Agent, or Firm* — Wayne C. Jaeschke, Jr.

(57) ABSTRACT

In one embodiment, an intramedullary nail has a proximal end and a distal end that are offset from one another along a distal direction. The nail has an outer surface and an inner surface. The inner surface defines a cannulation that extends into the proximal end towards the distal end. The nail defines a bone-anchor fixation hole that extends into the outer surface and entirely through the nail. The nail also defines a receptacle that is proximate to the bone-anchor fixation hole and open to the cannulation such that the receptacle is configured to receive a locator of a targeting system therein from the cannulation, where the locator includes at least one of a sensor and a field generator. The receptacle is at least partially defined by a stop that limits an insertion depth of the locator within the nail along the distal direction.

10 Claims, 11 Drawing Sheets

(56) References Cited

U.S. PATENT DOCUMENTS

| | | | |
|---|---|---|---|
| 2009/0177080 A1* | 7/2009 | Kristan | A61B 17/1707 600/424 |
| 2010/0274121 A1* | 10/2010 | Ritchey | A61B 5/1127 600/424 |
| 2013/0131679 A1* | 5/2013 | Janna | A61B 17/1707 606/62 |
| 2015/0305791 A1 | 10/2015 | Purohit | |

* cited by examiner

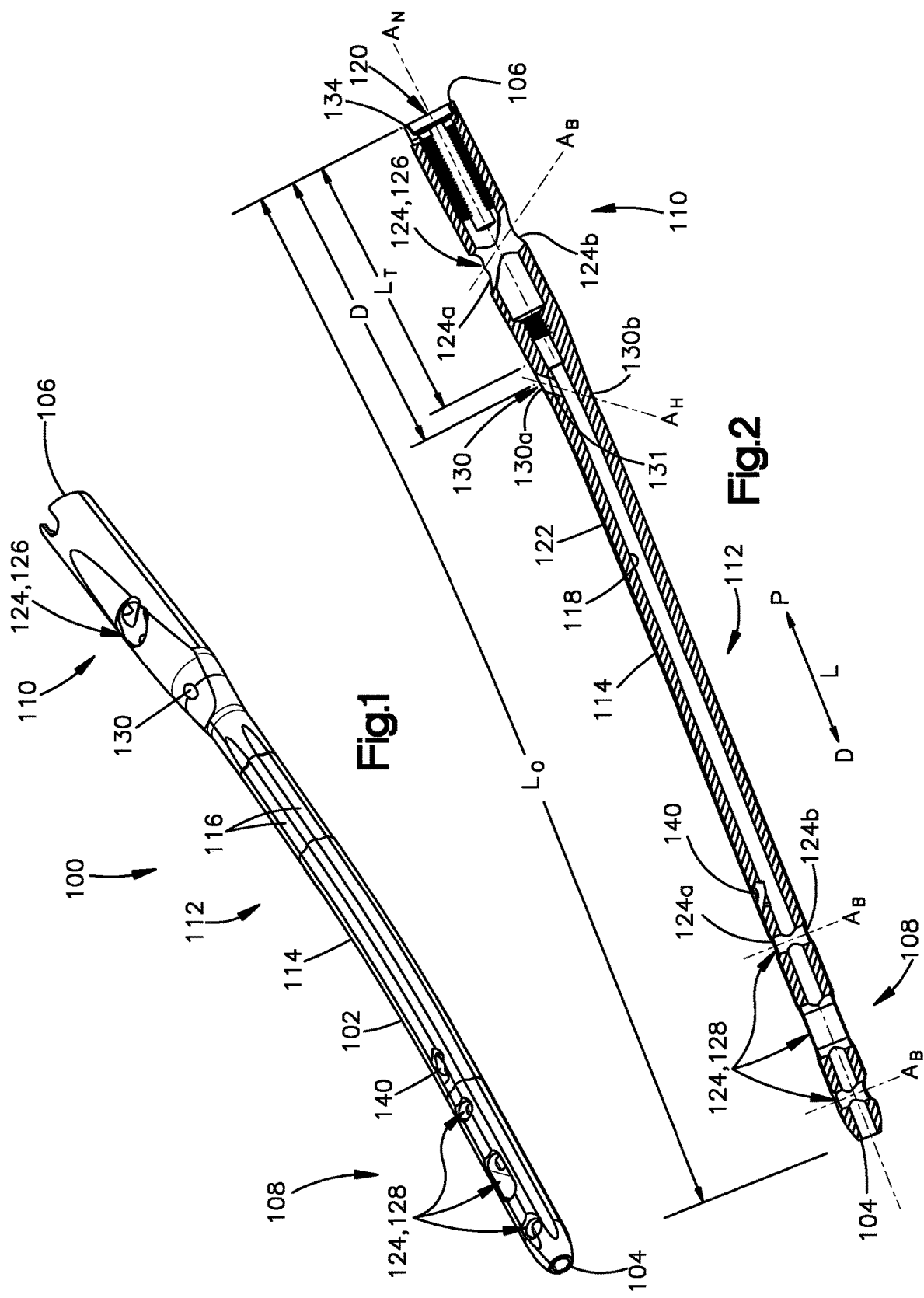

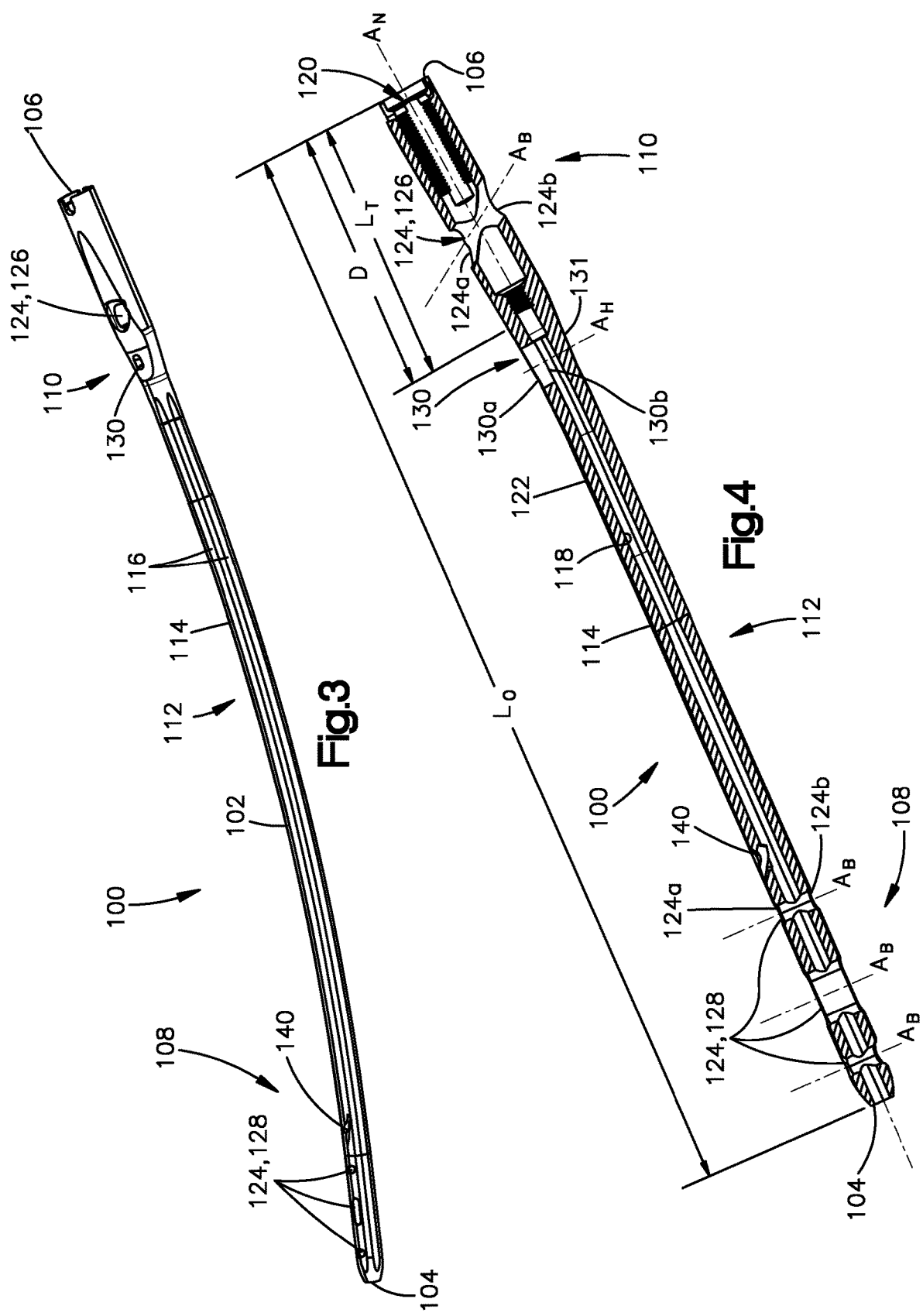

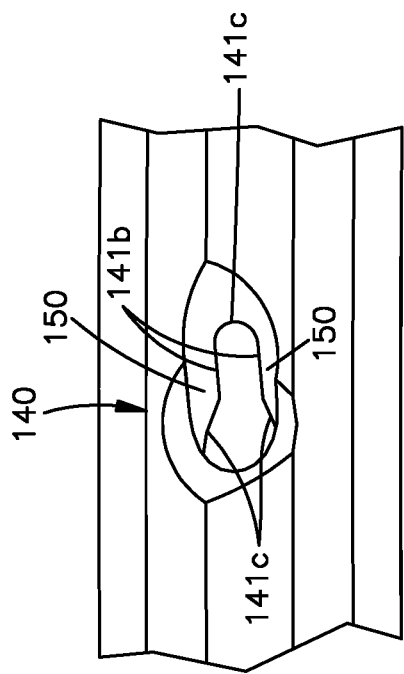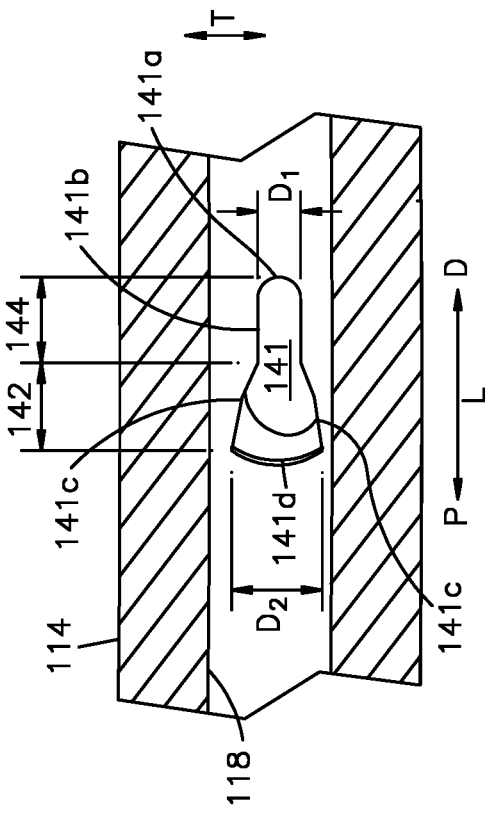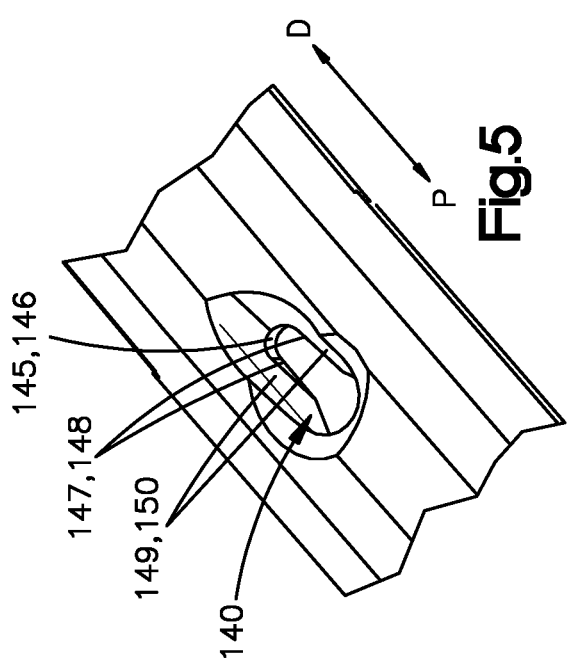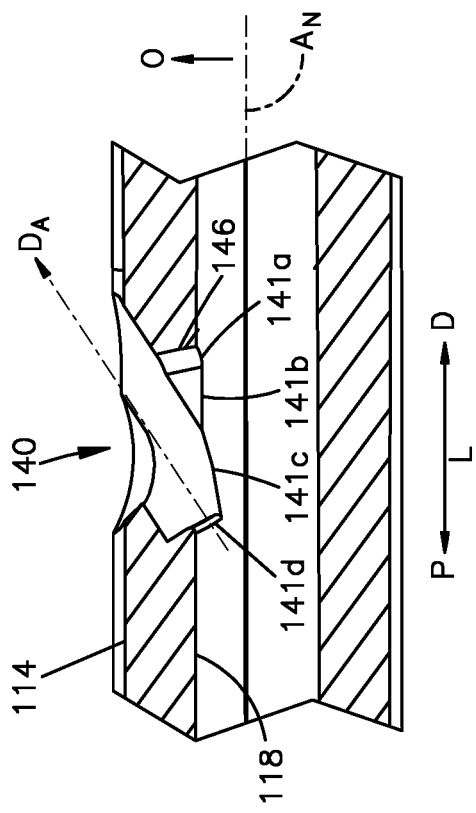

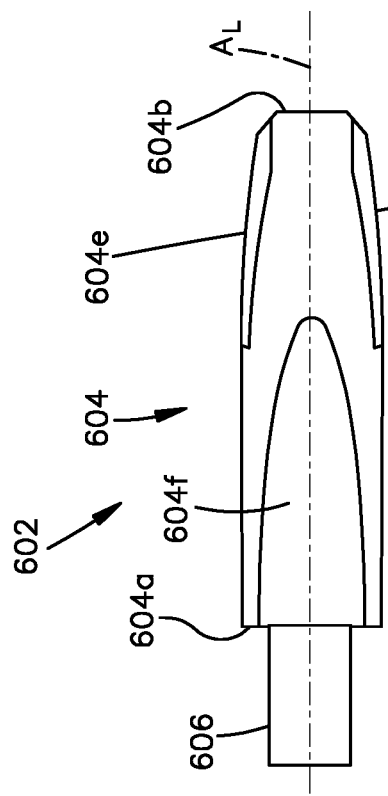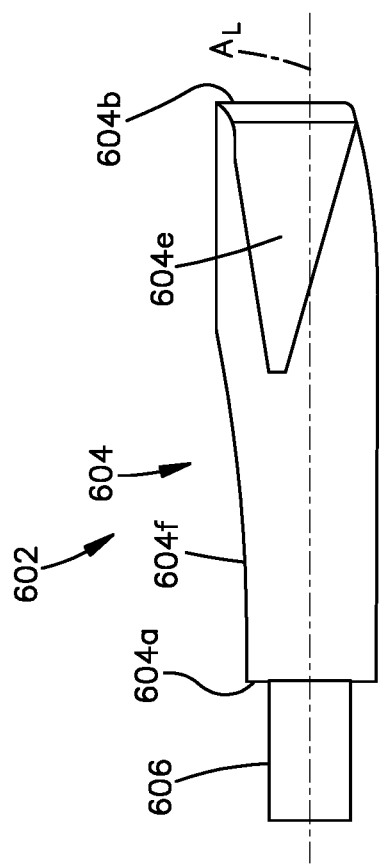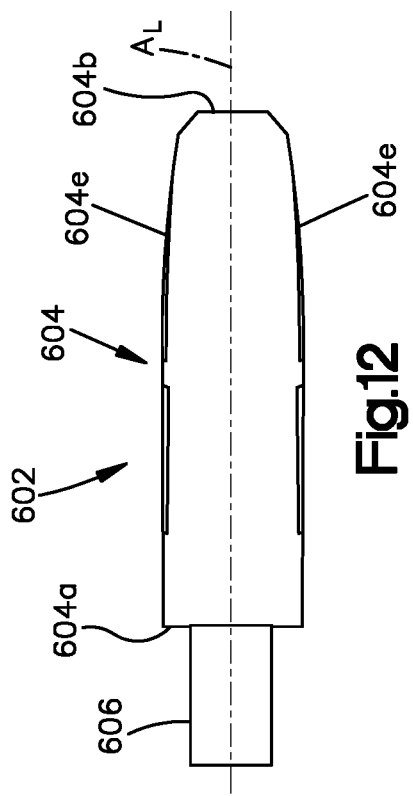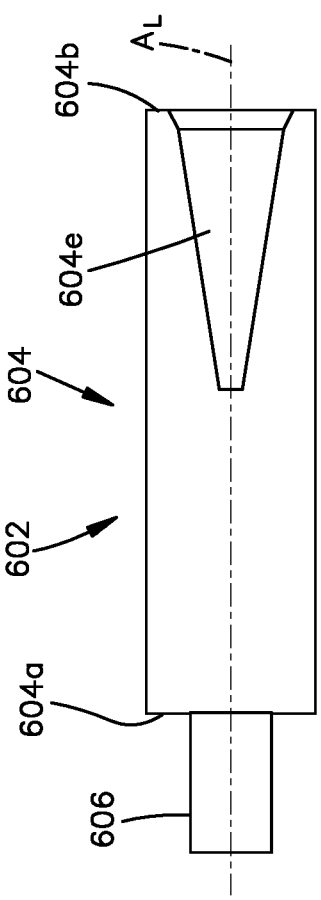

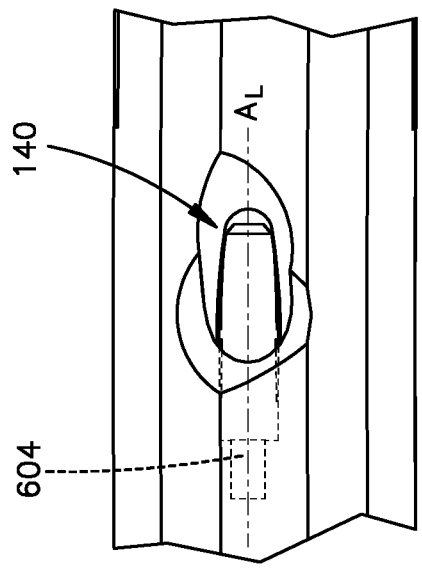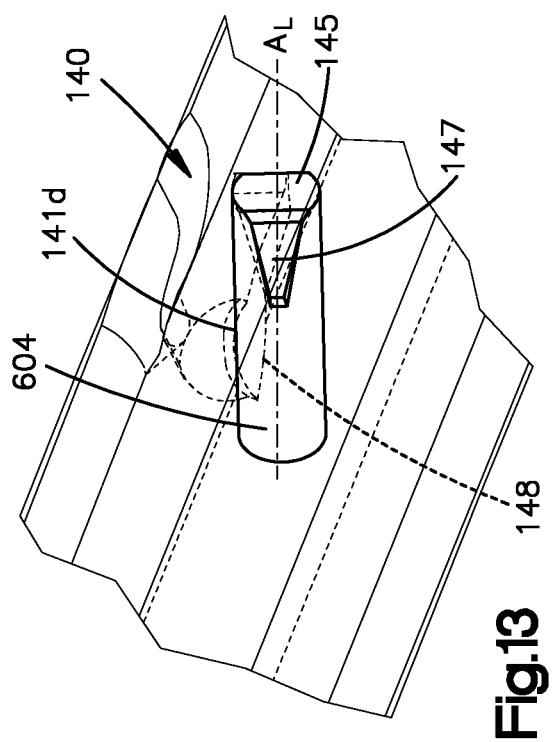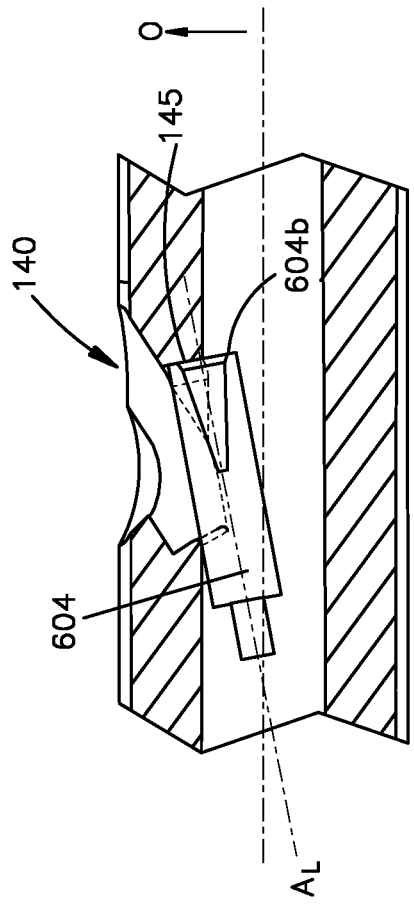

INTRAMEDULARY NAIL WITH RECEPATACLE FOR RECEIVING A TARETING DEVICE FOR TARGETING A BONE-ANCHOR FIXATION HOLE

TECHNICAL FIELD

The present disclosure relates to systems, assemblies, and methods for the insertion and fixation of a nail into an intramedullary canal of a bone.

BACKGROUND

Intramedullary nails are commonly used to treat fractures in long bones of the body such as fractures in femurs, tibias, and humeri. To treat such fractures, the intramedullary nail is inserted into a medullary canal of the long bone such that the nail spans across one or more fractures to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example embodiment, an intramedullary nail comprises a proximal body portion that defines a proximal end of the intramedullary nail, and a distal body portion, offset from the proximal body portion along a distal direction. The distal body portion defines a distal end of the intramedullary nail. The intramedullary nail comprises an outer surface that extends from the proximal end to the distal end, and an inner surface opposite the outer surface. The inner surface defines a cannulation that extends into the proximal end towards the distal end. The intramedullary nail defines a bone-anchor fixation hole that extends into the outer surface and through the inner surface such that the bone-anchor fixation hole is configured to receive a bone anchor therein. The receptacle is proximate to the bone-anchor fixation hole and open to the cannulation such that the receptacle is configured to receive a locator of a targeting system therein from the cannulation. The receptacle is defined by at least one guide that is configured to engage the locator so as to secure the locator in at least one of a predetermined longitudinal position and a predetermined rotational orientation relative to the bone-anchor fixation hole.

In another example embodiment, a system comprises a targeting instrument and an intramedullary nail. The targeting instrument comprises a locator that includes at least one of a sensor and a magnetic field generator. The intramedullary nail comprises a proximal body portion that defines a proximal end of the intramedullary nail, and a distal body portion, offset from the proximal body portion along a distal direction. The distal body portion defines a distal end of the intramedullary nail. The intramedullary nail comprises an outer surface that extends from the proximal end to the distal end, and an inner surface opposite the outer surface. The inner surface defines a cannulation that extends into the proximal end towards the distal end. The intramedullary nail defines a bone-anchor fixation hole that extends into the outer surface and through the inner surface such that the bone-anchor fixation hole is configured to receive a bone anchor therein. The intramedullary nail defines a receptacle that is proximate to the bone-anchor fixation hole and open to the cannulation such that the receptacle is configured to receive the locator therein from the cannulation. At least a portion of the receptacle has a shape that is complementary to a shape of at least a portion of the locator such that the receptacle is configured to engage the locator so as to secure the locator in at least one of a predetermined longitudinal position and a predetermined rotational orientation.

In another example embodiment, a method comprises a step of inserting a locator comprising at least one of a sensor and a field generator along a distal direction into a cannulation of an intramedullary nail that extends into a proximal end of the intramedullary nail towards a distal end of the intramedullary nail along the distal direction. The intramedullary nail defines a bone-anchor fixation hole that extends into an outer surface of the intramedullary nail such that the bone-anchor fixation hole is configured to receive a bone anchor therein. The method comprises a step of guiding the locator from the cannulation into a receptacle of the intramedullary nail that is proximate to the bone-anchor fixation hole such that the receptacle engages the locator so as to secure the locator in at least one of a predetermined longitudinal position and a predetermined rotational orientation.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1 shows a perspective view of an intramedullary nail according to one embodiment having a receptacle for receiving a locator of a targeting device;

FIG. 2 shows a cross-sectional side view of the intramedullary nail of FIG. 1;

FIG. 3 shows a perspective view of an intramedullary nail according to another embodiment having a receptacle for receiving a locator of a targeting device;

FIG. 4 shows a cross-sectional side view of the intramedullary nail of FIG. 3;

FIG. 5 shows an enlarged perspective view of the receptacle of FIGS. 1 to 4 according to one embodiment;

FIG. 6 shows a top plan view of the receptacle of FIG. 5;

FIG. 7 shows a cross-sectional side view of the receptacle of FIG. 5;

FIG. 8 shows a cross-sectional view bottom view of a portion of an intramedullary nail that shows a bottom of the receptacle of FIG. 5;

FIG. 9 shows side view of a locator of a targeting instrument according to one embodiment;

FIG. 10 shows top plan view of the locator of FIG. 9;

FIG. 11 shows side elevation view of a locator of a targeting instrument according to another embodiment;

FIG. 12 shows top plan view of the locator of FIG. 11;

FIG. 13 shows a perspective view of the receptacle of FIG. 5 with a locator received therein;

FIG. 14 shows a top plan view of the receptacle of FIG. 5 with a locator received therein;

FIG. 15 shows a cross-sectional side view of the receptacle of FIG. 5 with a locator received therein;

DETAILED DESCRIPTION OF ILLUSTRATIVE EMBODIMENTS

Figure 16:
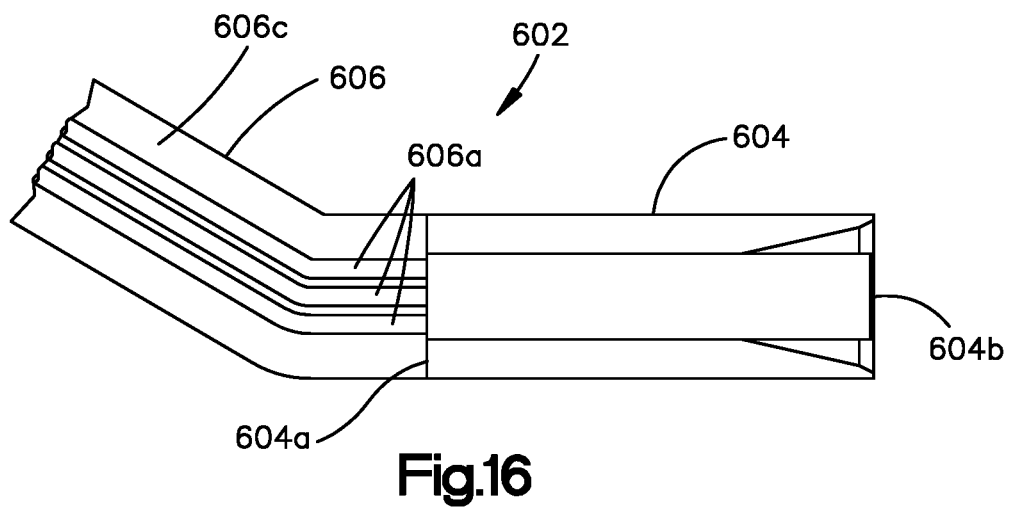
FIG. 16 shows a side view of a portion of a targeting instrument according to one embodiment, the targeting instrument including a locator supported by a cable.

Commonly, an intramedullary nail is implanted by driving the nail into a medullary canal of a long bone such as a tibia, fibula, humerus, or femur. Prior to insertion of the nail, the medial professional can enlarge the medullary canal to make room for the nail. For example, the medullary canal can be enlarged by inserting a reaming rod down the medullary canal, and guiding a reamer head with at least one cutting edge down the reaming rod such that the at least one cutting edge bores out the medullary canal. The reaming rod can be flexible so as to bend with the contour of the medullary canal. After enlarging the medullary canal, the intramedullary nail is then driven down into the enlarged medullary canal. In some cases, the reamer head can be removed, leaving the reaming rod in place, and the intramedullary nail can then be guided down the reaming rod into the medullary canal. As such, the reaming rod can be received in a cannulation of the intramedullary nail as the nail is driven down the reaming rod into the medullary canal.

To secure the intramedullary nail to the bone, the intramedullary nail can define at least one bone-anchor fixation hole that extends at least partially through the intramedullary nail. For example, the intramedullary nail can include at least one proximal bone-anchor fixation hole at a proximal portion of the intramedullary nail and at least one distal bone-anchor fixation hole at a distal portion of the intramedullary nail. The intramedullary nail can be secured to the bone by (1) drilling, for each bone-anchor fixation hole, a hole in the bone that aligns with the bone-anchor fixation hole, and (2) inserting, for each bone-anchor fixation hole, a bone anchor through the bone and into the bone-anchor fixation hole such that the bone anchor engages the bone on at least one side, such as opposed sides, of the intramedullary nail.

This procedure, however, can present several difficulties. For example, the proximal and distal bone-anchor fixation holes are not visible to the surgeon since the intramedullary nail is disposed inside the bone. Moreover, as the intramedullary nail is driven into the medullary canal, the intramedullary nail can bend by an undetermined amount. This bending can make it difficult to predict with accuracy the location and orientation of the at least one distal bone-anchor fixation hole. Therefore, a targeting system or systems can be employed to determine the location of each bone-anchor fixation hole, and/or align a cutting instrument such as a drill bit with each bone-anchor fixation hole. Once the location of a bone-anchor fixation hole is determined and/or the cutting instrument is aligned with the bone-anchor fixation hole, a hole can be drilled into the bone to the bone-anchor fixation hole. A bone anchor can subsequently be inserted through the bone and into the bone-anchor fixation hole.

One method of targeting the at least one distal bone-anchor fixation hole includes using fluoroscopy to obtain moving X-ray images of the position of the drill bit relative to the bone-anchor fixation hole in real-time. However, the use of fluoroscopy can over expose the patient, and particularly the surgeon who performs numerous such procedures, to harmful X-rays. As an alternative to fluoroscopy, the at least one distal bone-anchor fixation hole can be targeted using a targeting system having a locator that is positioned in the medullary nail proximate to the at least one distal bone-anchor fixation hole. The locator can include at least one of sensor and a field generator, such as a magnetic field generator. A cutting instrument, such as a drill, that includes another of the sensor and field generator is aligned with the at least one distal-bone anchor fixation hole based on a detection of the field generator by the sensor.

If the locator is not inserted in the nail in a known location and/or orientation, then the targeting system may need to be calibrated to account for the deviation in location and/or orientation. Otherwise, the hole could be drilled into the bone in an incorrect location and/or orientation. The following discussion relates to devices and methods for inserting a locator into an intramedullary nail proximate to at least one bone-anchor fixation hole in a known location and orientation so that the at least one bone-anchor fixation hole can be accurately targeted by the cutting instrument. Inserting the locator in such a manner can avoid a need to calibrate the targeting system, thereby saving time needed to perform the surgical procedure.

Figure 21:
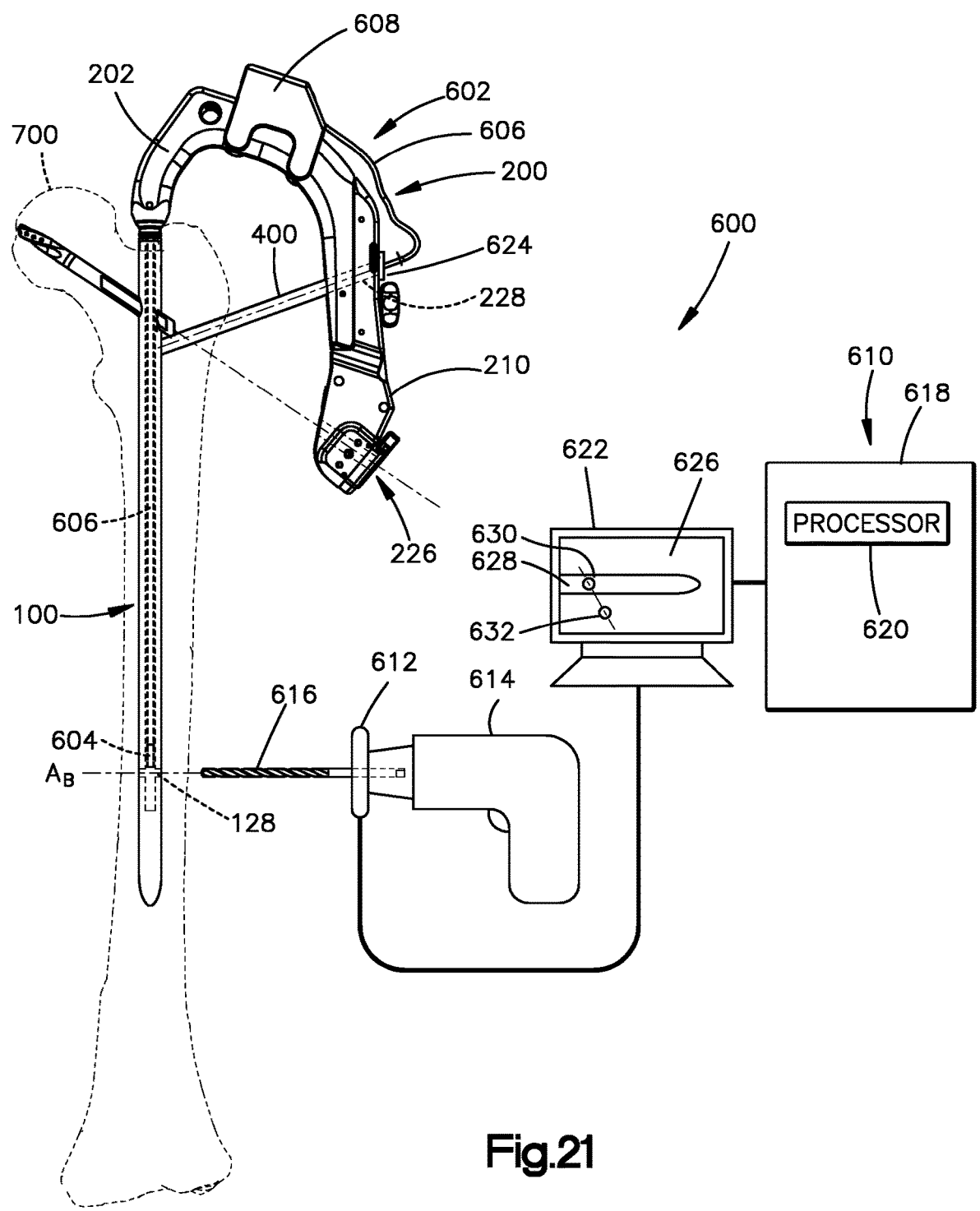
FIG. 21 shows a schematic diagram of an aiming system attached to an intramedullary nail that is received in a medullary canal of a bone and a targeting system used to locate a bone-anchor fixation hole of an intramedullary nail.

Referring briefly to FIGS. 1, 2, and 21, a system is shown that comprises an intramedullary nail 100 (FIGS. 1, 2, and 21) and a targeting instrument 602 (FIG. 9) that is configured to aid in alignment of a cutting instrument 616, such as a drill bit, with at least one bone-anchor fixation hole 124 (FIGS. 1 and 2) hidden beneath the surface of the bone 700. The targeting instrument 602 (FIG. 21), which can also be referred to as a probe, can include a locator 604 that is configured to be inserted into a cannulation 120 (FIGS. 1 and 2) of the intramedullary nail 100. The locator 604 can include at least one of a sensor and a field generator such as a magnetic field generator. The intramedullary nail 100 includes a receptacle 140 (FIGS. 1 and 2) that is proximate to the at least one bone-anchor fixation hole 124. The receptacle 140 is configured to receive at least a portion of the locator 604 therein as the targeting instrument 602 is inserted through the cannulation 120. The receptacle 140 can enable reliable positioning of the locator 604 relative to the at least one bone-anchor fixation hole 124 so that a location and orientation of the bone-anchor fixation hole 124 can be determined by a targeting system 600.

Turning to FIGS. 1 to 4, the intramedullary nail 100 has a distal end 104 and a proximal end 106 that are offset from one another. The distal end 104 can be considered to be an insertion end or leading end, and can define a first terminal or outermost end of the intramedullary nail 100. The proximal end 106 can be considered to be a trailing end and can define a second terminal or outermost end of the intramedullary nail 100. As used herein, the term "proximal end" refers to an end that is closer to the medical professional during the medical procedure than the distal end, and the term "distal end" refers to an end that is further from the medical professional during the medical procedure than the proximal end. Further, the term "proximal direction" refers to a direction that extends towards the medical professional during the medical procedure, while the term "distal direction" refers to a direction that extends away from the medical professional during the medical procedure. In some embodiments, the proximal and distal directions referred to herein can coincide with the anatomical proximal and distal directions of a patient's limb, respectively, such as in an antegrade approach where the intramedullary nail is inserted in an anatomical proximal end of a limb. However, embodiments of the disclosure are not so limited. Thus, in other embodiments, the proximal and distal directions referred to herein can coincide with the anatomical distal and proximal directions, respectively, such as in a retrograde approach where the intramedullary nail is inserted into an anatomical distal end of a limb.

The intramedullary nail 100 is elongate from the proximal end 106 to the distal end 104. For instance, the intramedullary nail 100 is substantially elongate along a central pathway that extends from the proximal end 106 to the distal end 104. In at least some embodiments, the central pathway can be defined by a central axis $A_N$ of the intramedullary nail 100 that extends from the proximal end 106 to the distal end 104. It will be appreciated that the central pathway or central axis $A_N$ of the intramedullary nail 100 can be straight or curved. Thus, the intramedullary nail 100 can be straight or curved as it extends along the central pathway or central axis $A_N$ from the proximal end 106 to the distal end 104. The intramedullary nail 100 can be inserted into a medullary canal of a long bone such that the central pathway or central axis $A_N$ extends along the length of the medullary canal.

The intramedullary nail 100 has a leading or distal body portion 108 and a proximal body portion 110 that are offset from one another. The intramedullary nail 100 also has an intermediate body portion 112 between the distal body portion 108 and the proximal body portion 110. The distal body portion 108 can extend from the distal end 104 of the intramedullary nail 100 towards the proximal end 106 along a proximal direction P, which can also be referred to as a trailing direction. Further, the proximal body portion 110 can extend from the proximal end 106 towards the distal end 104 along a distal direction D, which can also be referred to as an insertion direction. For example, the distal body portion 108 can extend from the distal end 104 to the intermediate body portion 112, and the proximal body portion 110 can extend from the proximal end 106 to the intermediate body portion 112. It will be understood that the distal direction D extends from the proximal end 106 towards the distal end 104, and the proximal direction P extends in a direction opposite the distal direction D (i.e., from the distal end 104 towards the proximal end 106).

In at least some embodiments, the proximal body portion 110 has a length $L_T$ that is less than half of an overall length $L_O$ of the intramedullary nail 100, such as less than or equal to one third of an overall length $L_O$ of the intramedullary nail 100, such as less than or equal to one quarter of the overall length $L_O$ of the intramedullary nail 100. Additionally, or alternatively, in at least some embodiments, the distal body portion 108 has a length $L_L$ that is less than half of an overall length $L_O$ of the intramedullary nail 100, such as less than or equal to one third of an overall length $L_O$ of the intramedullary nail 100, such as less than or equal to one quarter of the overall length $L_O$ of the intramedullary nail 100.

The intramedullary nail 100 has an outer surface 114 that extends from the distal body portion 108 to the proximal body portion 110. For instance, the outer surface 114 can extend from the proximal end 106 to the distal end 104. The outer surface 114 can define an outer-most perimeter of the intramedullary nail 100. Further, the outer surface 114 can have any suitable cross-sectional shape as desired. For example, the outer surface 114 can be substantially circular in cross section along a plane that is substantially perpendicular to the central pathway or central axis $A_N$. Additionally, or alternatively, the intramedullary nail 100 can define a plurality of recesses 116 that extend into the outer surface 114. The recesses 116 can be spaced circumferentially from one another around an outer perimeter of the intramedullary nail 100 and can be elongate as they extend between the distal body portion 108 and the proximal body portion 110 in accordance with the illustrated embodiments.

The intramedullary nail 100 has an inner surface 118 opposite the outer surface 114. Thus, the intramedullary nail 100 includes a tubular wall 122 between the inner surface 118 and the outer surface 114. The inner surface 118 defines a cannulation 120 that extends into the proximal end 106 in the distal direction D. The cannulation 120 can extend to the distal body portion 108. For example, the cannulation 120 can extend through the distal end 104. Alternatively, the cannulation 120 can terminate prior to the distal end 104 such as in the distal body portion 108 or the intermediate body portion 112. In at least some embodiments, the cannulation 120 can be configured (e.g., sized and shaped) so as to receive a rod, such as a reaming rod, therein as the intramedullary nail 100 is guided along the rod into the medullary canal of the bone. The cannulation 120 can extend along the central pathway or central axis $A_N$ of the intramedullary nail 100. The inner surface 118 can have a plurality of cross-sections along the central pathway or central axis $A_N$, each cross-section defined in a plane that is perpendicular to the central pathway or central axis $A_N$. The inner surface 118 in each cross-section can have any suitable cross-sectional shape as desired. For example, the inner surface 118 in each cross-section can define a cross-sectional shape that is closed such as a circle, oval, square, rectangle, or other shape.

The intramedullary nail 100 defines a plurality of bone-anchor fixation holes 124. Each bone-anchor fixation hole 124 is configured to receive a bone anchor so as to attach the intramedullary nail 100 to a bone. The bone-anchor fixation holes 124 can include at least one proximal bone-anchor fixation hole 126 and at least one distal bone-anchor fixation hole 128. Each bone-anchor fixation hole 124 can intersect the cannulation 120. Each bone-anchor fixation hole 124 is configured to receive a bone anchor that extends through the bone-anchor fixation hole 124 so as to attach the intramedullary nail 100 to a bone. In particular, each bone-anchor fixation hole 124 can extend into the outer surface 114 and at least partially, such as entirely, through the intramedullary nail 100. For instance, each bone-anchor fixation hole 124 can extend into the outer surface 114 on a first side of the intramedullary nail 100 and out of the outer surface 114 on a second side of the intramedullary nail 100, opposite the first side. Thus, each bone-anchor fixation hole 124 can extend from an opening 124a on a first side of the intramedullary nail 100 to an opening 124b on the second side of the intramedullary nail 100. As such, each bone-anchor fixation hole 124 can be considered to be a through hole, although embodiments of the disclosure are not limited to through holes. At least some of the bone-anchor fixation holes 124 can extend through the tubular wall 122 on a first side of the intramedullary nail 100 and through the tubular wall 122 on a second side of the intramedullary nail 100, opposite the first side.

Each bone-anchor fixation hole 124 extends through the intramedullary nail 100 along a central bone-anchor axis $A_B$ that is angled with respect to the central pathway or central axis $A_N$. For example, the central axis $A_N$ extends along a first direction adjacent each bone-anchor fixation hole 124, and each bone-anchor fixation hole 124 extends into the intramedullary nail 100 along a central axis $A_B$ that extends along a second direction, the second direction forming a non-zero angle with the first direction. In some embodiments, each bone-anchor fixation hole 124 extends through the intramedullary nail 100 along a central axis $A_B$ that forms a non-zero angle, such as a right angle or an oblique angle, with the central pathway or central axis $A_N$. Each bone-anchor fixation hole 124 can be unthreaded or can include internal threading to receive external threading of a bone anchor.

The plurality of bone-anchor fixation holes 124 includes at least one proximal bone-anchor fixation hole 126. Each of the at least one proximal bone-anchor fixation hole 126 extends entirely through the proximal body portion 110 of the intramedullary nail 100. In some embodiments, each of the at least one proximal bone-anchor fixation hole 126 extends into the intramedullary nail 100 at a distance from the distal end 106 that is less than or equal to one half of the overall length $L_O$ of the intramedullary nail 100, such as at a distance that is less than or equal to one third of the overall length $L_O$ of the intramedullary nail 100, such as a distance that is less than or equal to one quarter of the overall length $L_O$ of the intramedullary nail 100. Although only one proximal bone-anchor fixation hole 126 is shown, it will be understood that the intramedullary nail 100 can define a plurality of proximal bone-anchor fixation holes 126. In such embodiments, the plurality of proximal bone-anchor fixation holes 126 can be offset from one another along a longitudinal direction L that extends between the distal end 104 and the proximal end 106.

At least one proximal bone-anchor fixation hole 126 can have an axis $A_B$ that is aligned along the longitudinal direction L with the axis $A_B$ of an adjacent proximal bone-anchor fixation hole 126. For example, the axis $A_B$ of the at least one proximal bone-anchor fixation hole 126 can be in-plane with the axis $A_B$ of the adjacent proximal bone-anchor fixation hole 126. Thus, the openings 124a and 124b of the proximal bone-anchor fixation hole 126 can be aligned along the longitudinal direction L with the openings 124a or 124b of an adjacent proximal bone-anchor fixation hole 126. The central bone-anchor axis $A_B$ of each proximal bone-anchor fixation hole 126 can be parallel to the central bone-anchor axis $A_B$ of an adjacent one of the proximal bone-anchor fixation holes 126 or can be angularly offset from the central bone-anchor axis $A_B$ of an adjacent one of the proximal bone-anchor fixation holes 126 such that the central bone-anchor axes $A_B$ converge on one side of the intramedullary nail 100 and diverge on the other side.

Alternatively, the axis $A_B$ of at least one proximal bone-anchor fixation hole 126 can be angularly offset along the longitudinal direction L from the axis $A_B$ of an adjacent proximal bone-anchor fixation hole 126. For example, the axis $A_B$ of the at least one proximal bone-anchor fixation hole 126 can be out of plane with the axis $A_B$ of the adjacent proximal bone-anchor fixation hole 126. Thus, the openings 124a and 124b of each proximal bone-anchor fixation hole 126 can be out of alignment along the longitudinal direction L with the openings 124a and 124b of an adjacent proximal bone-anchor fixation hole 126. In other words, the openings 124a and 124b of each proximal bone-anchor fixation hole 126 at the outer surface 114 can be circumferentially offset from the openings 124a and 124b of an adjacent proximal bone-anchor fixation hole 126 at the outer surface 114. Thus, the central bone-anchor axis $A_B$ of each proximal bone-anchor fixation hole 126 can be at a non-zero angle relative to the central bone-anchor axis $A_B$ of an adjacent one of the proximal bone-anchor fixation holes 126.

The plurality of bone-anchor fixation holes 124 also includes at least one distal bone-anchor fixation hole 128. All of the at least one distal bone-anchor fixation holes 128 are offset from all of the at least one proximal bone-anchor fixation holes 126 along the longitudinal direction L. Each of the at least one distal bone-anchor fixation hole 128 extends entirely through the distal body portion 108 of the intramedullary nail 100. In some embodiments, each of the at least one distal bone-anchor fixation hole 128 extends into the intramedullary nail 100 at a distance from the distal end 104 that is less than one half of the overall length $L_O$ of the intramedullary nail 100, such as a distance that is less than or equal to one third of the overall length $L_O$ of the intramedullary nail 100, such as a distance that is less than or equal to one quarter of the overall length $L_O$ of the intramedullary nail 100. Although a plurality of distal bone-anchor fixation holes 128 is shown, it will be understood that the intramedullary nail 100 can define as few as one distal bone-anchor fixation hole 128. In embodiments having a plurality of distal bone-anchor fixation holes 128, the plurality of distal bone-anchor fixation holes 128 can be offset from one another along the longitudinal direction L.

Each distal bone-anchor fixation hole 128 can have an axis $A_B$ that is aligned along the longitudinal direction L with the axis $A_B$ of an adjacent distal bone-anchor fixation hole 128. For example, the distal bone-anchor fixation hole 128 and the adjacent distal bone-anchor fixation hole 128 can be in-plane with one another. Thus, the openings 124a and 124b of the distal bone-anchor fixation hole 128 can be aligned along the longitudinal direction L with the openings 124a and 124b of the adjacent distal bone-anchor fixation hole 128. Further, the central bone-anchor axis $A_B$ of each distal bone-anchor fixation hole 128 can be parallel to the central bone-anchor axis $A_B$ of an adjacent one of the distal bone-anchor fixation holes 128 or can be angularly offset from the central bone-anchor axis $A_B$ of an adjacent one of the distal bone-anchor fixation holes 128 such that the central bone-anchor axes $A_B$ converge on one side of the intramedullary nail 100 and diverge on the other side.

Alternatively, the axis $A_B$ of at least one distal bone-anchor fixation hole 128 can be angularly offset from the axis $A_B$ of an adjacent distal bone-anchor fixation hole 128 along the longitudinal direction L. For example, a distal bone-anchor fixation hole 128 and an adjacent distal bone-anchor fixation hole 128 can be out of plane with one another. As such, the openings 124a and 124b of each distal bone-anchor fixation hole 128 can be out of alignment along the longitudinal direction L with the openings 124a and 124b of an adjacent distal bone-anchor fixation hole 128. In other words, the openings 124a and 124b of each distal bone-anchor fixation hole 128 can be circumferentially offset from the openings 124a and 124b of an adjacent distal bone-anchor fixation hole 128. Thus, the central bone-anchor axis $A_B$ of each distal bone-anchor fixation hole 128 can be at a non-zero angle relative to the central bone-anchor axis $A_B$ of an adjacent one of the distal bone-anchor fixation holes 128.

Moreover, the axis $A_B$ of at least one distal bone-anchor fixation hole 128 can be aligned with the axis $A_B$ of a proximal bone-anchor fixation hole 126 along the longitudinal direction L. For example, the axis $A_B$ of a distal bone-anchor fixation hole 128 can be in-plane with the axis $A_B$ of a proximal bone-anchor fixation hole 126. As such, the openings 124a and 124b of the distal bone-anchor fixation hole 128 are aligned with the openings 124a and 124b of the proximal bone-anchor fixation hole 126 along the longitudinal direction L. Alternatively, the axis $A_B$ of at least one distal bone-anchor fixation hole 128 can be angularly offset from the axis $A_B$ of an adjacent proximal bone-anchor fixation hole 126. For example, the axis $A_B$ of a distal bone-anchor fixation hole 128 can be out of plane with the axis $A_B$ of a proximal bone-anchor fixation hole 126. As such, the openings 124a and 124b of the distal bone-anchor fixation hole 128 can be out of alignment with the openings 124a and 124b of the proximal bone-anchor fixation hole 126 along the longitudinal direction L. In other words, the openings 124a and 124b of the distal bone-anchor fixation hole 128 can be circumferentially offset from the openings 124a and 124b of an adjacent proximal bone-anchor fixation hole 126. Thus, the central bone-anchor axis $A_B$ of the distal bone-anchor fixation hole 128 can be at a non-zero angle relative to the central bone-anchor axis $A_B$ of the proximal bone-anchor fixation hole 126.

With continuing reference to FIGS. 1 to 4, the intramedullary nail 100 includes a receptacle 140 that is configured to receive at least a portion of the locator 604 (FIG. 21) of the targeting instrument 602. The receptacle 140 is configured to secure the locator 604 in a predetermined longitudinal position, and optionally a predetermined rotational orientation, relative to a select one of the bone-anchor fixation holes 124 that is to be targeted. As used herein, a longitudinal position refers to a position along the longitudinal direction L. The receptacle 140 is proximate to the select one of the bone-anchor fixation holes 124 that is to be targeted. For instance, the receptacle 140 can be closer to the select one of the bone-anchor fixation holes 124 than it is to one or more, up to all, of the other of the bone-anchor fixation holes 124. Preferably, the receptacle 140 is offset from the select one of the bone-anchor fixation holes 124 along the proximal direction P so that a cable 606 (see FIG. 21) of the targeting instrument 602 does not pass through the select bone-anchor fixation hole 124 as a cutting instrument is being targeted through the select bone-anchor fixation hole 124. The select bone-anchor fixation hole 124 can be a distal bone-anchor fixation hole 128, such as a proximalmost one of the at least one distal bone-anchor fixation holes 128. Thus, the receptacle 140 can be disposed at the distal body portion 108 of the intramedullary nail 100. It will be understood that, in alternative embodiments, the select bone-anchor fixation hole 124 can be a proximal bone-anchor fixation hole 126 to target the proximal bone-anchor fixation hole 126. In such alternative embodiments, the receptacle 140 could be disposed at the proximal body portion 108.

The receptacle 140 is open to the cannulation 120 such that the receptacle 140 is configured to receive at least a portion of the locator 604 of the targeting instrument 602 therein as the targeting instrument 602 is inserted into the cannulation 120. The receptacle 140 defines an opening that can extend into the inner surface 118 towards the outer surface 114 along an outer direction O so as to define an opening 141 at the inner surface 118. The outer direction O can be substantially perpendicular to the longitudinal direction L. In at least some embodiments, the receptacle 140 can extend through the outer surface 114, thereby allowing the locator 604 to push debris out of the receptacle 140 as the locator 604 is received in the receptacle 140. Conversely, the receptacle 140 can extend into the outer surface and terminate at the cannulation 120. The receptacle 140 can be angled towards the distal end 104 of the intramedullary nail 100 as the receptacle 140 extends from the inner surface 118 towards the outer surface 114. Thus, the receptacle 140, such as a proximal end of the receptacle 140, can extend from the inner surface 118 along a direction that is angularly offset from the central axis $A_N$ of the intramedullary nail 100. For example, the receptacle 140 can extend from the inner surface 118 along a direction that is offset between zero and 90 degrees from the central axis $A_N$, such as between 30 and 60 degrees from the central axis $A_N$. The receptacle 140 can extend at an angle less than 90 degrees so as to allow the locator 604 to translate more easily into the receptacle 140. The receptacle 140 can be a simple through hole. However, in alternative embodiments, the receptacle 140 can have other configurations.

Turning to FIGS. 5 to 11, the receptacle 140 is shown in which the receptacle 140 can have a keyed relationship with the locator 604 so as to secure the locator 604 in a predetermined longitudinal position and a predetermined rotational orientation relative to the select bone-anchor fixation hole 124. The receptacle 140 can have a proximal portion 142, and a distal portion 144 that is offset from the proximal portion 142 along the distal direction D. The receptacle 140 can be configured to receive at least a portion of the locator 604 along a path that extends from the cannulation 120, through the proximal portion 142, and into the distal portion 144. The proximal portion 142 can be angled as it extends from the inner surface 118 towards the distal end 104 of the intramedullary nail 100 as described above. The proximal portion 142 can be configured to align the locator 604 in the predetermined rotational orientation. For example, the proximal portion 142 can engage the locator 604 so as to cause the locator 604 to rotate into the predetermined rotational orientation. The distal portion 144 can be configured to secure the locator 604 in the predetermined longitudinal position and the predetermined rotational orientation when the locator 604 is aligned in the predetermined longitudinal position and the predetermined rotational orientation. At least a portion of each of the receptacle 140 and the locator 604, such as the distal portion 144 of the receptacle 140 and the distal end 604b of the locator 604, can have complementary shapes that are configured to engage one another so as to fix the locator in the predetermined rotational orientation. For example, the distal portion 144 can have a non-circular cross-section that is configured to engage a non-circular cross-section of the locator 604 so as to fix the rotational orientation of the locator 604.

The receptacle 140 can be defined by at least one guide that is configured to secure the locator in at least one of a predetermined longitudinal position and a predetermined rotational orientation relative to the bone-anchor fixation hole. The at least one guide of the intramedullary nail 100 can include a stop 145 that is configured to engage the locator 604 so as to limit an insertion depth of the locator 604 within the intramedullary nail 100 along the distal direction D. Thus, the stop 145 can be configured to engage the locator 604 so as to prevent the locator 604 from moving along the distal direction D. In other words, the stop 145 is configured to secure the locator 604 in the predetermined longitudinal position when the locator 604 engages the stop 145. The stop 145 can at least partially define the receptacle 140, such as the distal portion 144 of the receptacle 140. The stop 145 can face the proximal direction P. The stop 145 can be defined by at least one of an edge and a surface of the intramedullary nail 100. For example, the stop 145 can be defined by a stop edge 141*a* that at least partially defines the inner opening 141, such as a distal end of the inner opening 141. In some embodiments, the stop 145 can be defined by a stop surface 146 that extends from the stop edge 141*a* towards the outer surface 114 of the intramedullary nail 100. It will be understood that alternative embodiments of the disclosure can be implemented without the stop edge 141*a* or the stop surface 146.

The at least one guide of the intramedullary nail 100 can include at least one fixation guide 147 that is configured to secure the locator 604 in a predetermined rotational orientation. The at least one fixation guide 147 can be configured to engage the locator 604 so as to rotationally fix the locator 604. In other words, the at least one fixation guide 147 is configured to secure the locator 604 in the predetermined rotational orientation when at least one fixation guide 147 engages the locator 604. The at least one fixation guide 147 can at least partially define the receptacle 140, such as the distal portion 144 of the receptacle 140. Each of the at least one fixation guide 147 can be defined by at least one of an edge and a surface of the intramedullary nail 100. For example, each fixation guide 147 can be defined by a guide edge 141*b* that at least partially defines the inner opening 141. In some embodiments, each fixation guide 147 can be defined by a guide surface 148 that extends from the guide edge 141*b* towards the outer surface 114 of the intramedullary nail 100. The guide surface 148 can be substantially planar, although other configurations are contemplated. It will be understood that alternative embodiments of the disclosure can be implemented without the guide edge 141*b* or the guide surface 148.

In one example, the at least one fixation guide 147 can include a pair of opposing fixation guides 147 that are configured to engage opposing sides of the locator 604. The opposing fixation guides 147 can be offset from one another along a transverse direction T. The transverse direction T can be substantially perpendicular to the distal direction D and to the outward direction O that extends from the inner surface 118 of the intramedullary nail 100 to the outer surface 114 of the intramedullary nail 100. The distal portion 144 can have a dimension $D_1$ from one of the opposing fixation guides 147 to the other one of the fixation guides 147 along the transverse direction T. In at least one embodiment, the opposing fixation guides 147 can be substantially parallel to one another, although embodiments of the disclosure are not so limited. The opposing fixation guides 147 can at least partially define the distal portion 144 of the receptacle 140 therebetween.

The stop 145 can extend between the opposing fixation guides 147, such as from one of the opposing fixation guides 147 to the other one of the opposing fixation guides 147. The opposing fixation guides 147 can extend from the stop 145 along the proximal direction P. Together, the opposing fixation guides 147 and the stop 145 can define a perimeter of the distal portion 144. The opposing fixation guides 147 and the stop 145 can together define a non-circular shape that is configured to engage a non-circular cross-section of the locator 604 so as to prevent the locator 604 from rotating relative to the receptacle 140.

The at least one guide of the intramedullary nail 100 can include at least one alignment guide 149. The at least one alignment guide 149 can be configured to engage the locator 604 so as to rotate the locator 604 into the predetermined rotational orientation. For example, the alignment guide 149 can be configured to rotate the locator 604 so as to align opposing sides of the locator 604 with corresponding fixation guides 147 of the receptacle 140 as the locator 604 is translated from the proximal portion 142 to the distal portion 144. Thus, when the locator 604 is received in an orientation that is not aligned with the distal portion 144, the at least one alignment guide 149 can rotate the locator 604 so as to rotationally align the opposing sides of the locator 604 with the at least one fixation guide 147.

The at least one alignment guide 149 can at least partially define the proximal portion 142 of the receptacle 140. Each alignment guide 149 can be defined by at least one of an alignment edge 141*c* and an alignment surface 150. For example, each alignment guide 149 can be defined by an alignment edge 141*c* that at least partially defines the inner opening 141. In some embodiments, each alignment guide 149 can be defined by an alignment surface 150 that extends from the alignment edge 141*c* towards the outer surface 114 of the intramedullary nail 100. It will be understood that alternative embodiments of the disclosure can be implemented without the at least one alignment edge 141*c* or the at least one alignment surface 150.

In one example, the at least one alignment guide 149 can include a pair of opposing alignment guides 149. The opposing alignment guides 149 can be offset from one another along the transverse direction T. The opposing alignment guides 149 can be defined by opposing alignment edges 141*c* that at least partially define a proximal portion of the inner opening 141 therebetween. In at least some embodiments, the opposing alignment guides 149 can be defined by a pair of opposing alignment surfaces 150 that at least partially define the proximal portion 142 of the receptacle 140 therebetween.

The at least one alignment guide 149 can be offset from the at least one fixation guide 147 along the proximal direction P. The at least one alignment guide 149 can be disposed at the proximal portion 142 of the receptacle 140, and the at least one fixation guide 147 can be disposed at the distal portion 144. Each alignment guide 149 can extend from a proximal end of the recess 140 to a respective one of the fixation guides 147. The at least one alignment guide 149 can at least partially define the receptacle 140, such as a proximal end of the receptacle 140. The receptacle 140, such as a proximal portion 142 of the receptacle 140, can have a dimension $D_2$ from one of the opposing alignment guides 149 to the other one of the alignment guides 149 along the transverse direction T. The dimension $D_2$ can decrease along the distal direction D. Thus, the opposing alignment guides 149 can converge towards one another as they extend along the distal direction D such that the dimension $D_2$ of the decreases. Stated differently, the proximal portion 142 of the receptacle 140 can be tapered inwardly as it extends from the proximal end of the receptacle 140 towards the distal portion 144. The converging alignment guides 149 can engage the locator 604 so as to cause the locator 604 to rotate to the predetermined rotational orientation.

In at least some embodiments, the intramedullary nail 100 can include a pivot edge 141*d* that is configured to engage the locator 604 such that the locator 604 rotates about the pivot edge 141*d* as the locator 604 is received in the receptacle 140. The pivot edge 141*d* can at least partially define the receptacle 140, such as the proximal portion 142 of the receptacle 140. The pivot edge 141*d* can face the distal direction D. The pivot edge 141*d* can at least partially define the inner opening 141, such as a proximal end of the inner opening 141. The pivot edge 141*d* can be shaped so as to conform to a shape of the locator 604. For example, the pivot edge 141*d* can be curved so as to conform to a curved surface of the locator 604, although it will be understood that the pivot edge 141d can have other shapes. The pivot edge 141d can extend between the opposed alignment guides 149, such as from one of the alignment guides 149 to the other one of the alignment guides 149. The opposing alignment guides 149 can extend from the pivot edge 141d along the distal direction D. Together, the opposing alignment guides 149 and the pivot edge 141d can define a perimeter of the proximal portion 142. The opposing alignment guides 149, the pivot edge 141d, the opposing fixation guides 147, and the stop 145 can together define a perimeter of the inner opening 141.

Turning now to FIGS. 9 to 15, the targeting instrument 602 comprises a locator 604 that includes at least one of a sensor and a field generator. The field generator can be a magnetic field generator such as a permanent magnet or electromagnet. The locator 604 has a proximal end 604a, and a distal end 604b that is offset from the proximal end 604a along an axis $A_L$ of the locator 604. The axis $A_L$ can be a central axis that extends along a geometric center of the locator 604. It will be understood, however, that some embodiments might not have a geometric center, and therefore, the axis $A_L$ will not extend along the geometric center. At least a portion of the locator 604 can be tapered inwardly as the locator 604 extends from the distal end 604b to the proximal end 604a. Tapering of the locator 604 can make it easier for the locator 604 to be guided into the receptacle 604. The distal end 604b can be configured to engage the stop 145 of the receptacle 140 when the locator 604 is received in the receptacle 140. The locator 604 has an outer surface 604c that extends from the proximal end 604a to the distal end 604b. The outer surface 604c can be curved as it extends about the axis $A_L$. Thus, the outer surface 604c can have a substantially cylindrical shape.

In some embodiments, the locator 604 can include a housing that defines the outer surface 604c, wherein the housing houses the at least one of the sensor and the field generator. For example, sensor or field generator can be enclosed in an outer surface that can be in turn disposed in the housing of the locator 604. Thus, the sensor or field generator can be retrofitted to include the housing of the locator 604. In other embodiments, the outer surface 604c of the locator 604 can be an outer surface of the sensor or field generator. Thus, the sensor or field generator itself can be designed to include the outer surface 604c.

The locator 604 can include at least one fixation guide 604e that is configured to secure the locator 604 aid in orienting the locator 604 in the predetermined rotational orientation. The at least one fixation guide 604e can be configured to engage the at least one fixation guide 147 of the receptacle 140 so as to rotationally fix the locator 604. In at least one embodiment, each fixation guide 147 can be defined by a surface. The surface can be configured to conform to the at least one fixation guide 147. For example, the surface can be substantially planar so as to engage a planar surface of the at least one fixation guide 147, although other configurations are contemplated. In one example, the at least one fixation guide 604e can include a pair of opposing fixation guides 604e that are configured to engage opposing fixation guides 147 of the receptacle 140. The opposing fixation guides 604e can be offset from one another along a transverse direction T when the opposing fixation guides 604e engage the opposing fixation guides 147 of the receptacle 140.

In some embodiments, as shown in FIGS. 9 and 10, the locator 604 can have a depression 604f at the proximal end 604a of the locator 604. The depression 604 can be sized and shaped so as to enable the locator 604 to more easily make turns as the locator 604 is inserted into the intramedullary nail and the receptacle 604. For example, the depression 604 can be sized and shaped so as to enable the locator 604 to turn more easily from the cannulation 120 into the receptacle 140. The depression 604 can be rotationally offset from the fixation guides 604e. For example, the depression 604 can be disposed between the fixation guides 604e with respect to a rotational direction about the central axis $A_L$.

Referring to FIGS. 13 to 15, as described above, the receptacle 140 can be configured to fix the locator 604 in a predetermined longitudinal position. Thus, as shown in FIG. 15, the stop 145 of the receptacle 140 can be configured to abut the distal end 604b of the locator 604b so as to fix the locator 604 in the predetermined longitudinal position. The stop 145 can be configured to limit movement of the locator 604 along the distal direction D.

The receptacle 140 can also be configured to rotate the locator 604 into a predetermined rotational orientation and then fix the locator 604 in the predetermined rotational orientation. In particular, the receptacle 140 can be configured to rotate the locator 604 in at least one plane, such as at least two planes. The at least one plane can include a first plane that extends along the outward direction O and the longitudinal direction L. Thus, the receptacle 140 can be configured to rotate the distal end 604b of the locator 604 outwardly relative to the proximal end 604a of the locator 604. In particular, the pivot edge 141d can be engage the locator 604 as the locator 604 is received in the receptacle 140 so as to cause the distal end 604b of the locator 604 to rotate outwardly relative to the proximal end 604a of the locator 604 in the first plane. In some embodiments, the stop 145 of the receptacle 140 can be configured to engage, such as mate with, the distal end 604b of the locator so as to limit the angle of rotation in the first plane.

The at least one plane can include a second plane that is perpendicular to the axis $A_L$ of the locator 604. Thus, the receptacle 140 can be configured to rotate the locator 604 about the axis $A_L$. In particular, a first one of the alignment guides 149 can be configured to rotate the locator 604 along a first rotational direction about the axis $A_L$ when the locator 604 engages the first one of the alignment guides 149. A second one of the alignment guides 149 can be configured to rotate the locator 604 along a second rotational direction, opposite the first rotational direction, about the axis $A_L$ when the locator 604 engages the second one of the alignment guides 149. Thus, the opposing alignment guides 149 can be configured to correct a rotational angle of the locator 604 that deviates on either side of the predetermined rotational orientation. In some embodiments, the alignment guides 149 can be configured to rotate the locator 604 to the predetermined rotational orientation as long as the locator 604 is received at the proximal portion 142 within a predetermined range of angles, such as within ±45 degrees of the predetermined rotational orientation, such as within ±30 degrees of the predetermined rotational orientation. Stated differently, each alignment guide 149 can be configured to rotate the locator 604 by up to 45 degrees so as to align the locator 604 in the predetermined orientation, such as by up to 30 degrees. Once the locator 604 is aligned in the predetermined rotational orientation, the at least one fixation guide 147 of the receptacle 140 engages the at least one fixation guide 604e of the locator 604 so as to fix the locator in the predetermined rotational orientation.

Figure 17:
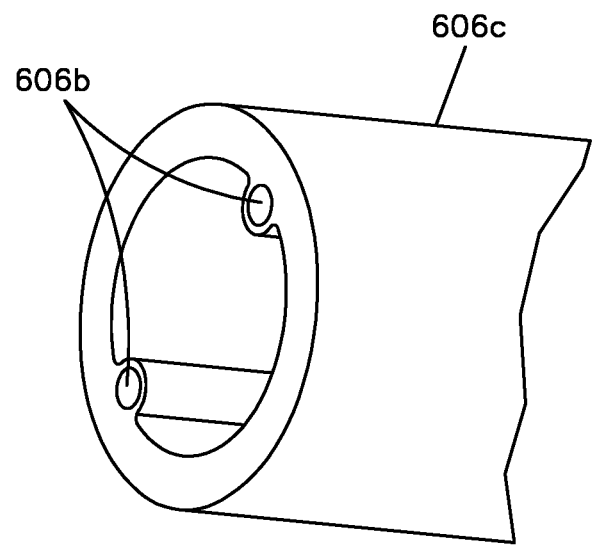
FIG. 17 shows an enlarged perspective view of an end of a sheath of the cable of FIG. 16 according to one embodiment.

Turning to FIGS. 16 and 17, the targeting instrument 602 has a cable 606 that extends from the locator 604, such as the proximal end 604a of the locator 604. Thus, the locator 604 can be supported by the cable 606, for example, at the end of the cable 606. The cable 606 can comprise at least one wire. For example, in embodiments in which the locator 604 comprises a sensor, the cable 606 can comprise at least one cable 606a that is configured to communicate electrical signals between the sensor and a computing device 610 (see FIG. 21). In the embodiments in which the locator 604 is an electromagnet, the cable 606 can comprise at least one cable 606a that is configured to communicate power to the electromagnet. In embodiments in which the locator 604 is a permanent magnet, the cable 606 need not comprise a wire that is configured to communicate signals or power.

The cable 606 can have a stiffness that is sufficient to push the locator 604 through the cannulation 120 of the intramedullary nail 100 and into the receptacle 140, without the cable 606 folding or bending back upon itself within the cannulation 120. For example, the cable 606 can have at least one stiffener that prevents the cable 606 from folding upon itself within the cannulation 120. The stiffener can have a strength that is sufficient to counter any frictional forces between the locator 604 and the intramedullary nail 100 as the locator 604 is pushed through the cannulation 120. Further, the stiffener can have a strength that is sufficient to counter any forces exerted on the targeting instrument 602 as the cable 606 is bent through the entrance into the intramedullary nail 100 and as the locator 604 is rotated into the receptacle 140.

The stiffener can include at least one of a stiffener cable 606b and a sheath 606c. The sheath 606c can be configured to support at least one of a cable 606a and a stiffener cable 606b therein. The sheath 606c can have a stiffness that prevents the cable 606 folding or bending back upon itself within the cannulation 120. The sheath 606c can be formed from a non-conductive, such as an insulative, material. In some embodiments, the at least one stiffener cable 606b can include a pair of stiffener wires 606b that are offset from one another along a radial direction. The pair of stiffener wires 606b can have a stiffness that is sufficient to prevent the cable 606 from twisting about a longitudinal axis of the cable 606. The pair of wires 606b can have a strength that is sufficient to counter any forces exerted on the targeting instrument 602 that would cause the cable 606 to twist as the cable is through the cannulation 120 and into the receptacle 140.

Figure 18:
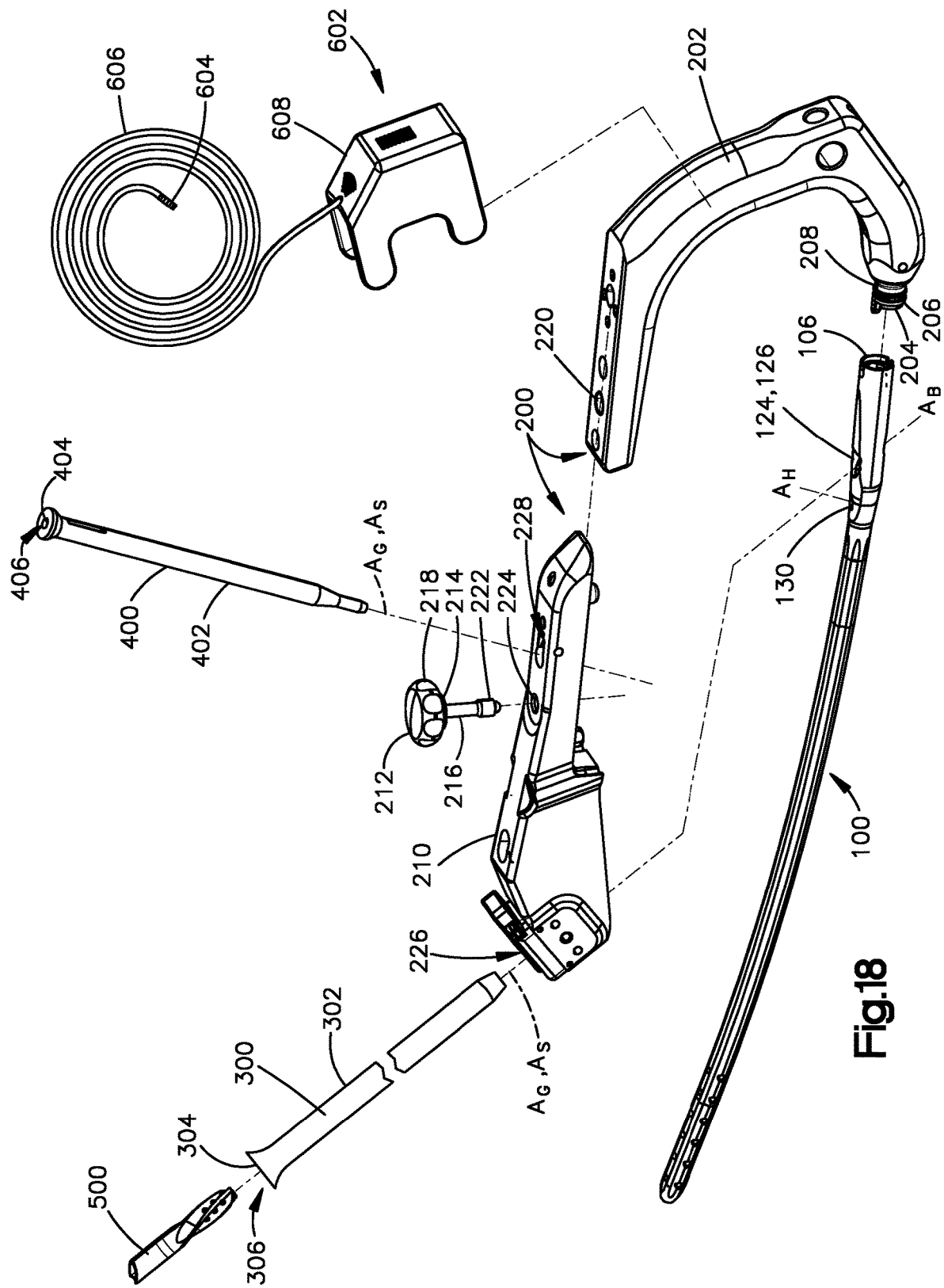
FIG. 18 shows an exploded perspective view of an intramedullary nail with an aiming system and a targeting instrument according to one embodiment.

In some embodiments, at least a portion of the cable 606, such as at least one of the sheath 606c and the at least one stiffener cable 606b, comprises a shape memory material. The shape memory material, and hence the at least one of the sheath 606c and stiffener cable 606b, can be biased towards a curved, such as a coiled, configuration as shown in FIG. 18. Thus, when the targeting instrument 602 is inserted into the intramedullary nail 100, the cable 606 can be biased along the outward direction O against the inner surface 118 of the intramedullary nail 100. Biasing the cable 606 in such a manner can enable the locator 604 to be received in the receptacle 140 more reliably.

Referring back to FIGS. 1 to 4, a bone anchor that extends through bone-anchor fixation holes at the proximal end of the nail may pass through a cannulation that extends into the proximal end of the nail towards the distal end. In such case, the bone anchor intersects the cannulation, thereby restricting access to the cannulation from the proximal end of the nail. To provide access to the cannulation before or after insertion of the proximal bone anchor, an access hole 130 can be provided in the intramedullary nail 100 between the proximal end 106 and the distal end 104 of the intramedullary nail 100. The access hole 130 can provide access insertion of the targeting instrument 602. Alternatively, the insertion instrument 602 can be inserted into the intramedullary nail 100 via the cannulation opening at the proximal end 106 of the intramedullary nail 100.

In one example, the intramedullary nail 100 can define the access hole 130 at the intermediate body portion 112. Thus, the access hole 130 can be between all of the at least one distal bone-anchor fixation holes 128 on the distal body portion 108 and all of the at least one proximal bone-anchor fixation holes 126 on the proximal body portion 110. In some embodiments, the intramedullary nail 100 can be devoid of any distal bone-anchor fixation holes 128 between the access hole 130 and the proximal body portion 110. Additionally, or alternatively, the intramedullary nail 100 can be devoid of any proximal bone-anchor fixation holes 126 between the access hole 130 and the distal body portion 108. Thus, in some embodiments, the access hole 130 can be closer to a distal-most one of the proximal bone-anchor fixation holes 128 than to any other bone-anchor fixation holes 124. The access hole 130 can extend into the intramedullary nail 100 at a location that is closer to the proximal end 106 than the distal end 104. For example, the access hole 130 can extend into the intramedullary nail 100 between the proximal body portion 110 and a midpoint of the intramedullary nail 100. As another example, the access hole 130 can extend into the intramedullary nail 100 at a distance D from the proximal end 106 that is less than one third of the overall length $L_O$ of the intramedullary nail 100. As yet another example, the access hole 130 can extend into the intramedullary nail 100 at a distance D from the proximal end 106 that is less than one fourth of the overall length $L_O$ of the intramedullary nail 100. The intramedullary nail 100 can be devoid of bone-anchor fixation holes between the access hole 130 and a midpoint of the central axis $A_N$.

The access hole 130 extends only partially through the intramedullary nail 100. For instance, the access hole 130 extends along an access hole central axis $A_H$ and into the outer surface 114 between the distal body portion 108 and the proximal body portion 110. Further, the access hole 130 extends through the inner surface 118 such that the access hole 130 terminates at the cannulation 120 and is in communication with the cannulation 120. In other words, the access hole 130 can extend through the tubular wall 122 on a first side of the intramedullary nail 100 and terminate at the tubular wall 122 on a second of the intramedullary nail 100, opposite the first side, without extending through the tubular wall 122 on the second side. Thus, the central axis $A_H$ intersects the tubular wall 122 on the second side of the intramedullary nail 100. Further, the intramedullary nail 100 can define an outer opening 130a at the outer surface 114 and an inner opening 130b at the inner surface 118, and the access hole 130 can extend from the outer opening 130a to the inner opening 130b.

The central axis $A_H$ of the access hole 130 can be in-plane with the at least one of a proximal bone-anchor fixation hole 126 and a distal bone-anchor fixation hole 128 along the longitudinal direction L. Thus, the outer opening 130a of the access hole 130 can be aligned with an opening 124a or 124b of at least one of a proximal bone-anchor fixation hole 126 and a distal bone-anchor fixation hole 128 along the longitudinal direction L. Alternatively, the central axis $A_H$ of the access hole 130 can be angularly offset from the central axis $A_B$ of at least one of a proximal bone-anchor fixation hole 126 and a distal bone-anchor fixation hole 128 along the longitudinal direction L. Thus, the outer opening 130a of the access hole 130 can be out of alignment with the openings 124a and 124b of the proximal bone-anchor fixation hole 126 and/or distal bone-anchor fixation hole 128 along the longitudinal direction L.

The access hole 130 extends into the intramedullary nail 100 along an access-hole central axis $A_H$. The nail-body central axis $A_N$ can extend along a first direction at a location adjacent the access hole 130, and the access hole central axis $A_H$ can extend along a second direction that forms a non-zero angle with the first direction. In some embodiments, and with specific reference to FIGS. 1 and 2, the second direction can form an oblique angle with the first direction. Further, in some such embodiments, the access-hole central axis $A_H$ can be angled with respect to the central pathway or central axis $A_N$. In particular, the access hole 130 can extend into the intramedullary nail 100 along an access-hole central axis $A_H$ that forms an oblique angle with the central pathway or central axis $A_N$. It will be understood, however, that in some embodiments the access-hole central axis $A_H$ need not intersect the central axis $A_N$. The access hole 130 can be angled towards the distal end 104 as the access hole 130 extends from the outer surface 114 to the inner surface 118. As such, the inner surface 131 that defines the access hole 130 is configured to guide the targeting instrument 602 towards the distal body portion 108 as the targeting instrument 602 is inserted into the access hole 130.

In other embodiments, and with specific reference to FIGS. 3 and 4, the nail-body central axis $A_N$ can extend along a first direction at a location adjacent the access hole 130, and the access hole central axis $A_H$ can extend along a second direction that forms a right angle with the first direction. In some such embodiments, the access hole 130 can form a right angle with the central pathway or central axis $A_N$. The targeting instrument 602 can be inserted into the access hole 130 along a path that is angled towards the distal body portion 108 as the path extends from the outer surface 114 to the inner surface 118 so as to direct the targeting instrument 602 towards the distal body portion 108 as the targeting instrument 602 is inserted into the access hole 130. In other words, rather than the access hole 130 directing the targeting instrument 602 towards the distal body portion 108, another device such as an aiming sleeve (see e.g., 400 of FIG. 18) or the user can angle the targeting instrument 602 as the instrument 602 is inserted into the access hole 130 so as to guide the targeting instrument 602 towards the distal body portion 108. In some embodiments, the access hole 130 can be angled towards the distal body portion 108 and an aiming sleeve 400 and the access hole 130 together can guide the instrument towards the distal body portion 108.

The access hole 130 can have any suitable cross-sectional shape in a plane that is perpendicular to the access-hole central axis $A_H$. For example, and with specific reference to FIGS. 1 and 2, the access hole 130 can have a cross-sectional shape that is substantially circular in a plane that is perpendicular to the access-hole central axis $A_H$. As another example, and with specific reference to FIGS. 3 and 4, the access hole 130 can have a cross-sectional shape that is substantially oblong in a plane that is perpendicular to the access-hole central axis $A_H$.

Turning now to FIG. 18, a system is shown with an intramedullary nail 100, an aiming system 200, and a targeting instrument 602. The aiming system 200 can include any combination of one or more, up to all, of (i) a handle 202, (ii) an aiming arm 210, (iii) a bone-anchor aiming sleeve 300, and (iv) an access-hole aiming sleeve 400. The aiming system 200 is configured to align tools or instruments with at least one of a proximal bone-anchor fixation hole 126 and the access hole 130. For example, when the aiming system 200 is attached to the intramedullary nail 100, the aiming system 200 can align at least one of a drill bit (not shown) and a bone anchor 500 with the at least one proximal bone-anchor fixation hole 126 so as to guide the at least one of a drill bit (not shown) and the bone anchor 500 towards the at least one proximal bone-anchor fixation hole 126. The bone anchor 500 can be a bone screw, such as a locking screw, or any other suitable bone anchor. In addition, or alternatively, when the aiming system 200 is attached to the intramedullary nail 100, the aiming system 200 can align at least one of a drill bit (not shown) and the targeting instrument 602 with the access hole 130 so as to guide the at least one of a drill bit (not shown) and instrument towards the access hole 130. Although one embodiment of an aiming system 200 is shown, it will be understood that other configurations of aiming systems can be employed. For instance, at least one of the handle 202 and aiming arm 210 can be configured in a manner other than that shown.

The handle 202 is configured to be held by an operator (human or machine) as the operator guides and forces the intramedullary nail 100 into the medullary canal of the bone. The handle 202 can include a connection end 204 configured to connect to the proximal end 106 of the intramedullary nail 100. The connection end 204 can include an engagement feature configured to couple to an engagement feature at the proximal end 106 of the intramedullary nail 100. For example, in one embodiment, the engagement feature of the handle 202 can include a shaft 206 having external threading 208 thereon, and the engagement feature of the intramedullary nail 100 can include internal threading 134 (see FIG. 2) on the inner surface 118 of the cannulation 120 of the intramedullary nail 100 at the proximal end 106. The shaft 206 can be sized and configured to be received in the cannulation 120 at the proximal end 106 of the intramedullary nail 100 such that the external threading 208 engages the internal threading 134 of the intramedullary nail 100. In alternative embodiments, the engagement features of the handle 202 and the intramedullary nail 100 can be engagement features other than the internal and external threading shown, the other engagement features being suitable for coupling the handle 202 to the intramedullary nail 100.

The at least one aiming arm 210 can be fixedly or removably attached to the handle 202 via any suitable fastener. Alternatively, the handle 202 can be monolithic with the aiming arm 210 such that the handle 202 and aiming arm 210 form a one-piece structure. The aiming system 200 can include a coupler 212 that removably attaches the aiming arm 210 to the handle 202. In one embodiment, the coupler 212 can have an abutment surface 214 and a shaft 216 that extends from the abutment surface 214 to a distal end of the shaft 216. The abutment surface 214 can be defined by a handgrip 218. The shaft 216 can have an engagement feature configured to engage an engagement feature of a bore 220 of the handle 202. Further, the shaft 216 is sized and configured to extend through a bore 224 of the aiming arm 210 into the bore 222 of the handle 202 such that the aiming arm 210 is trapped between the abutment surface 214 and the handle 202. In one example, the engagement feature of the shaft 216 can be external threading and the engagement feature of the bore 220 can be internal threading that is configured to engage the external threading of the shaft 216.

The aiming system 200 can define a guide hole 226 that is configured to guide at least one a drill bit (not shown) and the bone anchor 500 towards the at least one proximal bone-anchor fixation hole 126. The guide hole 226 can have a central axis $A_G$ that is substantially aligned with the central axis $A_B$ of the at least one proximal bone-anchor fixation hole 126 when the aiming system 200 is attached to the intramedullary nail 100. Additionally, or alternatively, the aiming system 200 can define a guide hole 228 that is configured to guide at least one of a drill bit and the targeting instrument 602 towards the access hole 130. The guide hole 228 can have a central axis $A_G$ that is substantially aligned with the central axis $A_H$ of the access hole 130 when the aiming system 200 is attached to the intramedullary nail 100.

The bone-anchor aiming sleeve 300 has a tubular body that includes an outer surface 302 and an inner surface 304. The outer surface 302 defines an outer perimeter of the sleeve 300 and is sized and configured to conform to the guide hole 226. The inner surface 304 is opposite the outer surface 302 and defines a cannulation 306 that extends entirely through the sleeve 300. The cannulation 306 is sized to receive at least one of a drill bit and the bone anchor 500. When the sleeve 300 is received in the guide hole 226 and the aiming system 200 is attached to the intramedullary nail 100, a central axis $A_S$ of the sleeve 300 can be substantially aligned with the central axis $A_G$ of the guide hole 226 and the central axis $A_B$ of the at least one proximal bone-anchor fixation hole 126. As such, the sleeve 300 is positioned and configured to guide at least one of the drill bit and the bone anchor 500 towards the at least one proximal bone-anchor fixation hole 126. It will be understood that, in alternative embodiments, the sleeve 300 can be integral with the aiming arm 210 or can be omitted.

Similarly, the access-hole aiming sleeve 400 has a tubular body that includes an outer surface 402 and an inner surface 404. The outer surface 402 defines an outer perimeter of the sleeve 400 and is sized and configured to conform to the guide hole 228. The inner surface 404 is opposite the outer surface 402 and defines a cannulation 406 that extends entirely through the sleeve 400. The cannulation 406 is sized to receive at least one of a drill bit and the targeting instrument 602. When the sleeve 400 is received in the guide hole 228 and the aiming system 200 is attached to the intramedullary nail 100, a central axis $A_S$ of the sleeve 400 can be substantially aligned with the central axis $A_G$ of the guide hole 228 and the central axis $A_H$ of the access hole 130. As such, the sleeve 400 is positioned and configured to guide at least one of the drill bit and the instrument towards the access hole 130. It will be understood that, in alternative embodiments, the sleeve 400 can be integral with the aiming arm 210 or can be omitted.

Referring now to FIGS. 18 and 21, embodiments of the disclosure can include a targeting system 600 (FIG. 21) that can be used to detect a location of at least one of a proximal bone-anchor fixation hole 126 and a distal bone-anchor fixation hole 128 hidden beneath the surface of the bone 700. The targeting system 600 can be implemented as described in U.S. Pat. No. 8,623,023, the teachings of which are hereby incorporated by reference as if set forth in their entirety herein. The targeting system 600 can include the targeting instrument 602 having the locator 604 and the cable 606 that supports the locator 604. In embodiments where the locator 604 comprises a sensor, the sensor can be a six degree of freedom sensor, although it will be understood that other sensors can be used. At least a portion of the targeting instrument 602, including the locator 604 and the cable 606, is sized to be received through the access hole 130, into the cannulation 120, and into the receptacle 140.

The targeting instrument 602 can optionally include a wireless communicator 608 that communicates with a computing device 610 positioned outside of the body. Alternatively, the targeting instrument 602 can be connected to the computing device 610 via a cable such that communications between the targeting instrument 602 and the computing device 610 occur over the cable. The wireless communicator 608 can include an antenna (not shown), a communications circuit (not shown) coupled to the antenna, and a power source such as a battery that can power at least one of the wireless communicator 608 and the locator 604. In one example, the wireless communicator 608 can be attached to a proximal end of the cable 606 and the locator 604 can be attached to a distal end of the cable 606.

The targeting system 600 can further include at least one of a computing system 610, a landmark identifier 612, and a cutting instrument 614 such as a drill having a drill bit 616. The landmark identifier 612 is used to detect a location of at least one of a proximal bone-anchor fixation hole 126 and a distal bone-anchor fixation hole 128. The landmark identifier 612 can include at least one of a sensor and a field generator. In one example, the field generator can include one or more induction coils that generate an electromagnetic field. The computing system 610 can include a processor 620 and a feedback device 622 that provides to the user at least one of (i) a visual feedback (e.g., via a monitor or lights), (ii) an audio feedback (e.g., via a speaker), and (iii) a tactile feedback. The processor 620 and the feedback device 622 can be implemented in separately or the feedback device 622 can be implemented in a shared housing 618 with the processor 620.

Figure 19:
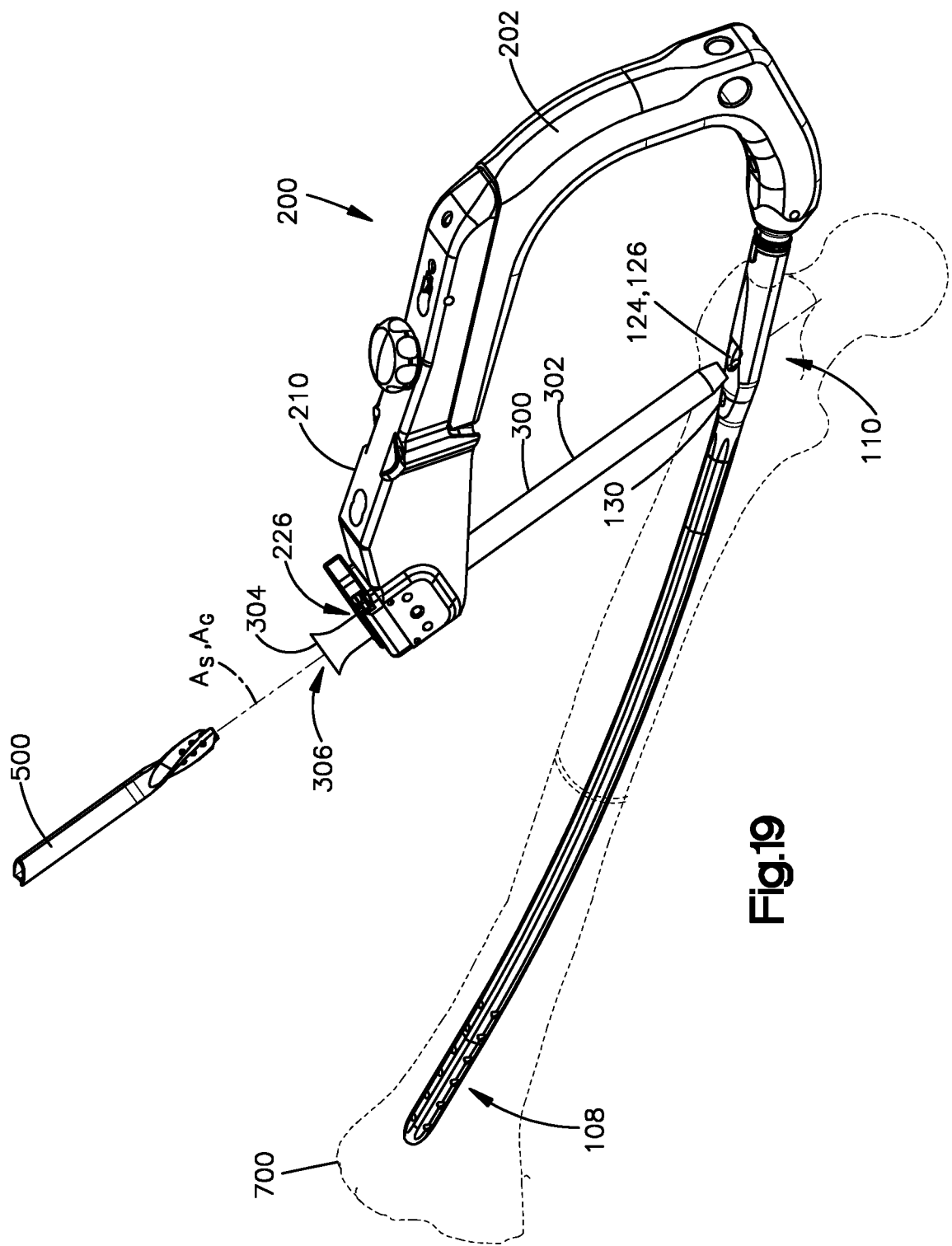
FIG. 19 shows a perspective view of an aiming guide attached to an intramedullary nail that is received in a medullary canal of a bone, the aiming guide supporting a bone-anchor aiming sleeve receiving a drill bit.

Turning now to FIGS. 19 to 22, a method 800 of implanting the intramedullary nail 100 will now be described. In step 802 of FIG. 10, the intramedullary nail 100 is inserted into the medullary canal of a bone 700 such that the intramedullary nail 100 is elongate along the medullary canal from the distal body portion 108 of the intramedullary nail 100 to the proximal body portion 110 of the intramedullary nail 100 as shown in FIG. 19. In one embodiment, the handle 202 of the aiming system 200 is coupled to the proximal end 106 of the intramedullary nail 100, and the operator holds onto the handle 202 to drive the intramedullary nail 100 into the medullary canal of the bone 700. The aiming arm 210 can be attached to the handle 202 before or after the nail 100 is driven into the bone. In some embodiments, a rod, such as a reaming rod, can be inserted into the medullary canal, and the intramedullary nail 100 can be guided along the rod such that the rod is received in the cannulation 102 of the intramedullary nail 100.

Optionally, in step 804, a proximal bone anchor 500 can be inserted into at least one proximal bone-anchor fixation hole 126 such that the proximal bone anchor 500 extends through the cannulation 120 of the intramedullary nail 100. As a result, the bone anchor 500 intersects the cannulation 120 so as to at least partially obstruct the proximal end of the cannulation 120. According to one embodiment, step 804 can be performed as follows and with reference to FIG. 19. The aiming arm 210 is attached to the handle 202 (if not already attached). The bone-anchor aiming sleeve 300 is received in the guide hole 226 of the aiming system 200 such that the central axis $A_S$ of the sleeve 300 is substantially aligned with both the central axis $A_G$ of the guide hole 226 and the central axis $A_B$ of the at least one proximal bone-anchor fixation hole 126. A cut is made in the skin of the patient (before or after receiving the sleeve 300) at a point where the central axis $A_G$ of the guide hole 226 intersects the skin, and the sleeve 300 can be advanced into the skin towards the bone 700. A cutting instrument, such as a drill bit 616 of a drill 614 (shown in FIG. 21), can then be inserted into the bone-anchor aiming sleeve 300 and guided towards the proximal bone-anchor fixation hole 126 so as to cut a bore that extends into the bone to the proximal bone-anchor fixation hole 126. A bone anchor 500 such as a locking screw or other suitable bone anchor is driven through the bore in the bone and into the proximal bone-anchor fixation hole 126 so as to secure the proximal end 106 of the intramedullary nail 100 to the bone 700.

Figure 20:
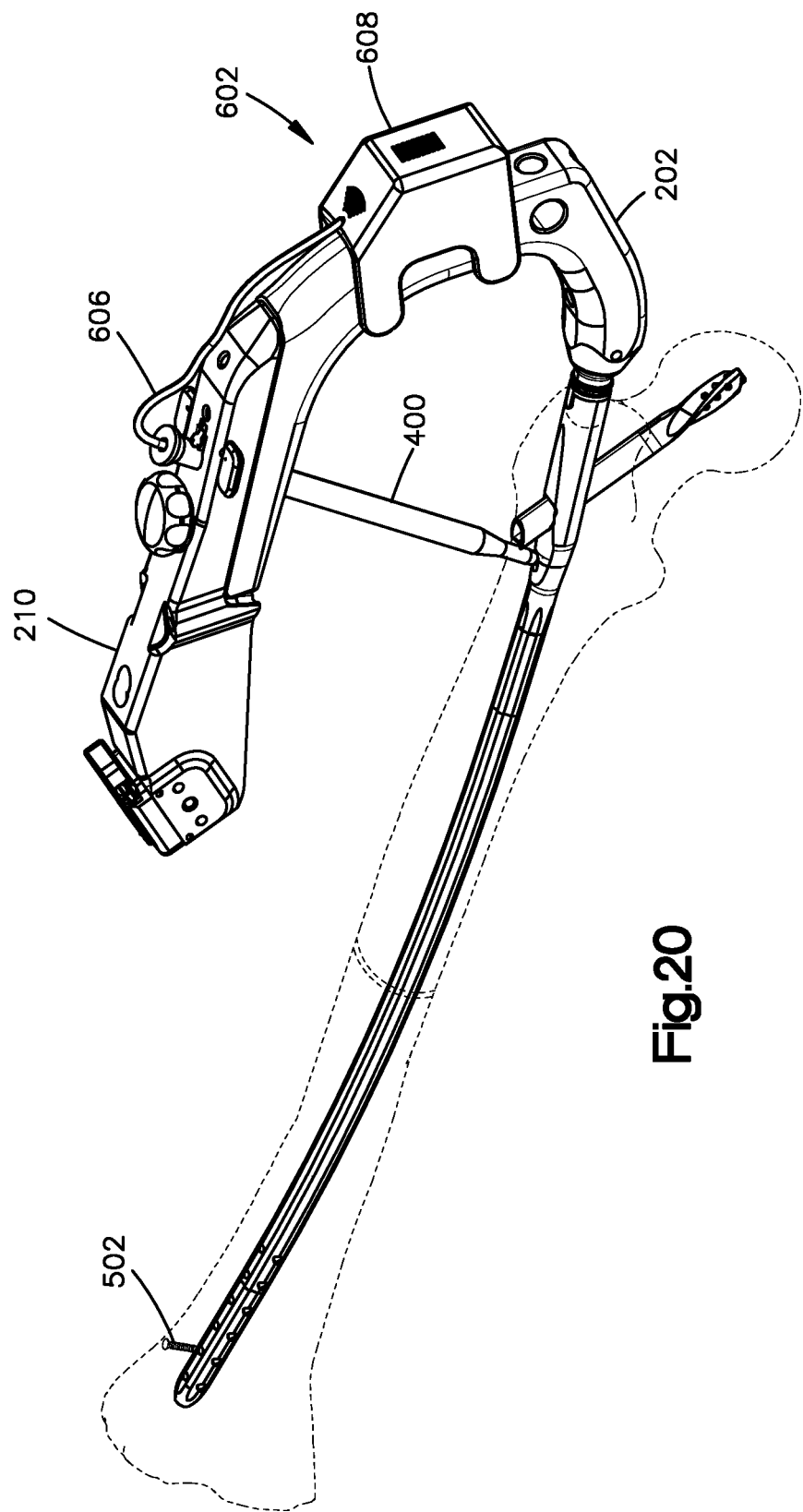
FIG. 20 shows a perspective view of an aiming guide attached to an intramedullary nail that is received in a medullary canal of a bone, the aiming guide supporting an access-hole aiming sleeve and a targeting instrument.
Figure 22:
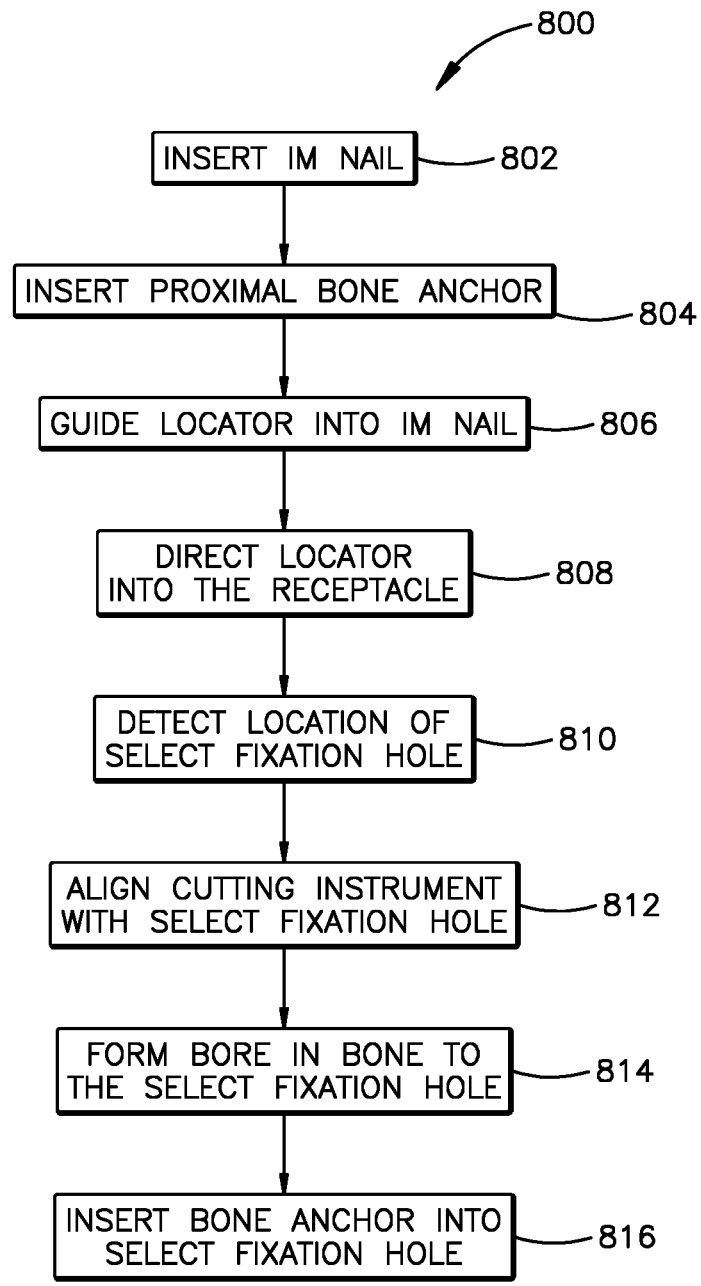
FIG. 22 shows a simplified flow diagram of a method of implanting an intramedullary nail according to one embodiment.

Referring more specifically to FIGS. 20-22, in step 806, the targeting instrument 602 is guided into the cannulation 120 of the intramedullary nail 100 through the access hole 130 that extends into the outer surface 114 of the intramedullary nail 100 between the at least one proximal bone-anchor fixation hole 126 and the at least one distal bone-anchor fixation hole 128. According to one embodiment, step 806 can be performed as follows and with reference to FIGS. 20 and 21. The aiming sleeve 400 is received in the guide hole 228 of the aiming system 200 (assuming it is not already received or is not integral with the aiming arm 210) such that the central axis $A_S$ of the sleeve 400 is substantially aligned with both the central axis $A_G$ of the guide hole 228 and the central axis $A_B$ of the access hole 130. A cut is made in the skin of the patient (before or after receiving the sleeve 400) at a point where the central axis $A_G$ of the guide hole 228 intersects the skin, and the sleeve 400 can be advanced into the skin towards the bone 700. A cutting instrument is then advanced through the sleeve 400 and towards the bone 700 so as to cut a bore in the bone 700 that extends to the access hole 130. Preferably, the bore in the bone has a central axis that is substantially aligned with the central axis $A_H$ of the access hole 130. The locator 604 of the targeting instrument 602 is then guided through the aiming sleeve 400 and into the access hole 130 of the intramedullary nail 100 by pushing the cable 606, and consequently the locator 604, into the aiming sleeve 400. Note that, in alternative embodiments, the locator 604 can be inserted into the intramedullary nail 100 through an opening in the proximal end 106 of the intramedullary nail 100 that is defined by the cannulation 120.

In step 808, the locator 604 of the targeting instrument 602 is directed along the cannulation 120 of the intramedullary nail 100 and into the receptacle 140. As the locator 604 is received in the receptacle 140, the locator 604 can pass through the proximal portion 142 of the receptacle 140 into the distal portion 144 of the receptacle 140. As the locator 604 passes through the proximal portion 142, the proximal portion 142 can rotate the locator 604 so as to align the locator 604 in the predetermined rotational orientation. For example, the locator 604 can engage the pivot edge 141d (shown in FIGS. 7 and 8), thereby causing the locator 604 to rotate in a plane that extends along the outward direction O and the longitudinal direction L. Thus, the receptacle 140 can be configured to rotate the distal end 604b of the locator 604 outwardly relative to the proximal end 604a of the locator 604. Additionally, or alternatively, the locator 604 can engage at least one of the alignment guides 149 (shown in FIGS. 5 and 6), thereby causing the locator 604 to rotate about the axis $A_L$ of the locator 604 (e.g., in a plane that is perpendicular to the axis $A_L$).

As the locator 604 is received into the distal portion 144 of the receptacle 140, the receptacle 140 can fix at least one of a rotational orientation and longitudinal position of the locator 604. For example, at least one fixation guide 604e of the locator 604 can engage at least one fixation guide 147 of the receptacle 140 thereby preventing the locator 604 from rotating about the axis $A_L$ of the locator 604. Additionally, or alternatively, a distal end 604b of the locator 604 can engage a stop 145 of the receptacle 140. The stop 145 can limit movement of the locator 604 along the distal direction D. Additionally, or alternatively, the stop 145 can limit a rotation of the locator 604 in the plane that extends along the outward direction O and the longitudinal direction L.

In step 810, and with reference to FIGS. 21 and 22, a location of the select bone-fixation hole 124 is detected based on a position of the locator 604. In some embodiments, the processor 620 can receive signals from at least one of (i) the locator 604 and (ii) the landmark identifier 612, and determine, based on the received signals, a current position and orientation of the landmark identifier 612 relative to the locator 604.

In step 812, the cutting instrument is aligned with the select bone-fixation hole 124 based on the detected location of the select bone-fixation hole 124. The cutting instrument 616 and the select fixation hole 124 can be aligned using feedback generated by the processor 620 and provided to the operator by the feedback device 622. For example, the processor 620 of the computing device 610 can generate a graphical user interface based on the determined current position and orientation of the drill 614 and the drill bit 616 relative to the select bone-anchor fixation hole 124, or based on a current position and orientation of another tool relative to another landmark. The graphical user interface can include a representative image 628 of the intramedullary nail 100 that includes a representative image 630 of the select bone-anchor fixation hole 124. The graphical user interface can also include a representation 632 of the drill bit 616. The operator can move the drill 614 relative to the distal bone-anchor fixation hole 128 until the representative images 628 and 630 of the intramedullary nail 100 and drill bit 616 are aligned. In alternative embodiments, the feedback device can provide instructions via an audio signal or lights (e.g., lighted arrows) to instruct the operator which direction(s) to move the drill 614 to align the drill bit 616 with the select fixation hole.

In step 814, a bore is cut into the bone 700 with the cutting instrument 614 such that the bore extends to the select bone-fixation hole. Preferably, the bore is substantially coaxial with the select fixation hole. In cutting the bore, the cutting instrument 614 can be advanced into the bone 700 a select distance. The select distance can be predetermined or can be determined during the operation. For example, the select distance can be determined based on relative positions of the cutting instrument 614 and the select bone-anchor fixation hole 124 (as determined from the position of the locator 604). Alternatively, the cutting instrument 614 can be provided with a stop or markings that can be used to determine when the cutting instrument 614 has advanced a predetermined distance.

Prior to cutting the bore, an incision can be made in the skin at the location of the select fixation hole. Additionally, a guide sleeve can be inserted into the incision towards the bone 700, and the guide sleeve can receive the cutting instrument 614 as the cutting instrument cuts the bore so as to prevent the cutting instrument 614 from damaging soft tissue. After cutting the bore in the bone 700, a bone anchor 502 (FIG. 8) is inserted in step 816 through the bore and into the select fixation hole 124 so as to secure the intramedullary nail 100 to the bone 700.

Although there has been shown and described the certain embodiments of the present disclosure, it will be readily apparent to those skilled in the art that modifications may be made thereto which do not exceed the scope of the appended claims. The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed:

1. An intramedullary nail, comprising:
   a proximal body portion that defines a proximal end of the intramedullary nail;
   a distal body portion, offset from the proximal body portion along a distal direction, and defining a distal end of the intramedullary nail;
   an outer surface that extends from the proximal end to the distal end;
   an inner surface opposite the outer surface, the inner surface defining a cannulation that extends into the proximal end towards the distal end, wherein the intramedullary nail defines:
      a bone-anchor fixation hole that extends into the outer surface and through the inner surface such that the bone-anchor fixation hole is configured to receive a bone anchor therein; and
      a receptacle that is proximate to the bone-anchor fixation hole and open to the cannulation such that the receptacle is configured to receive a locator of a targeting system therein from the cannulation, the locator including at least one of a sensor and a field generator, wherein the receptacle is defined by at least one guide that is configured to engage the locator so as to secure the locator in at least one of a predetermined longitudinal position and a predetermined rotational orientation relative to the bone-anchor fixation hole wherein the receptacle defines an aperture that extends into the inner surface towards the outer surface and is angled towards the distal end as the receptacle extends from the inner surface towards the outer surface.

2. The intramedullary nail of claim 1, wherein the receptacle extends into the inner surface towards the outer surface along an outward direction, and the at least one guide comprises a guide that is configured to engage the locator so as to rotate the locator in a plane that extends along the outward direction and the distal direction.

3. The intramedullary nail of claim 1, wherein the receptacle includes:
   a proximal portion configured to rotate the locator relative to the bone-anchor fixation hole so as to align the locator in the predetermined rotational orientation; and
   a distal portion that is offset from the proximal portion along the distal direction, the distal portion configured to secure the locator in the predetermined, longitudinal position and the predetermined rotational orientation.

4. The intramedullary nail of claim 3, wherein the distal portion has a non-circular cross-section that is configured to engage a non-circular cross-section of the locator so as to prevent the locator from rotating relative to the receptacle about an axis of the locator.

5. An intramedullary nail comprising:
   a proximal body portion that defines a proximal end of the intramedullary nail;

a distal body portion, offset from the proximal body portion along a distal direction, and defining a distal end of the intramedullary nail;

an outer surface that extends from the proximal end to the distal end;

an inner surface opposite the outer surface, the inner surface defining a cannulation that extends into the proximal end towards the distal end, wherein the intramedullary nail defines:

a bone-anchor fixation hole that extends into the outer surface and through the inner surface such that the bone-anchor fixation hole is configured to receive a bone anchor therein; and a receptacle that is proximate to the bone-anchor fixation hole and open to the cannulation such that the receptacle is configured to receive a locator of a targeting system therein from the cannulation, the locator including at least one of a sensor and a field generator, wherein the receptacle is defined by at least one guide that is configured to engage the locator so as to secure the locator in at least one of a predetermined longitudinal position and a predetermined rotational orientation relative to the bone-anchor fixation hole, wherein the at least one guide comprises at least one alignment guide that is configured to engage the locator so as to rotate the locator into the predetermined rotational orientation.

6. The intramedullary nail of claim 5, wherein the alignment guide is configured to engage the locator so as to rotate the locator relative to the bone-anchor fixation hole about an axis of the locator that extends from a proximal end of the locator to a distal end of the locator.

7. A system, comprising:

a targeting instrument comprising a locator that includes at least one of a sensor and a magnetic field generator; and an intramedullary nail, comprising:

a proximal body portion that defines a proximal end of the intramedullary nail;

a distal body portion, offset from the proximal body portion along a distal direction and defining a distal end of the intramedullary nail;

an outer surface that extends from the proximal end to the distal end;

an inner surface opposite the outer surface the inner surface defining a cannulation that extends into the proximal end towards the distal end, wherein the intramedullary nail defines:

a bone-anchor fixation hole that extends into the outer surface and through the inner surface such that the bone-anchor fixation hole is configured to receive a bone anchor therein; and a receptacle that is proximate to the bone-anchor fixation hole and open to the cannulation such that the receptacle is configured to receive the locator therein from the cannulation, at least a portion of the receptacle having a shape that is complementary to a shape of at least portion of the locator such that the receptacle is configured to engage the locator so as to secure the locator in at least one of a predetermined longitudinal position and a predetermined rotational orientation, wherein the targeting instrument comprises a cable that supports the locator at an end thereof and at least a portion of the cable comprises a shape memory material such that the cable is biased towards a coiled configuration.

8. The system of claim 7, wherein the receptacle extends into the inner surface towards the outer surface and is angled towards the distal end as the receptacle extends from the inner surface towards the outer surface.

9. The system of claim 7, wherein the intramedullary nail comprises at least one alignment guide that at least partially defines the receptacle and is configured to engage the locator so as to rotate the locator into the predetermined rotational orientation.

10. A method, comprising:

inserting a locator comprising at least one of a sensor and a field generator along a distal direction into a cannulation of an intramedullary nail that extends into a proximal end of the intramedullary nail towards a distal end of the intramedullary nail along the distal direction, the intramedullary nail defining a bone-anchor fixation hole that extends into an outer surface of the intramedullary nail such that the bone-anchor fixation hole is configured to receive a bone anchor therein; and guiding the locator from the cannulation into a receptacle of the intramedullary nail that is proximate to the bone-anchor fixation hole such that the receptacle engages the locator so as to secure the locator in at least one of a predetermined longitudinal position and a predetermined rotational orientation wherein the guiding step comprises causing the locator to engage at least one alignment guide of the receptacle so as to rotate the locator into the predetermined rotational orientation.

\* \* \* \* \*